(12) United States Patent
Denham

(10) Patent No.: US 10,987,146 B2
(45) Date of Patent: Apr. 27, 2021

(54) BONE DEFECT REPAIR APPARATUS AND METHOD

(71) Applicant: NEXTREMITY SOLUTIONS, INC., Warsaw, IN (US)

(72) Inventor: Gregory J Denham, Warsaw, IN (US)

(73) Assignee: NEXTREMITY SOLUTIONS, INC., Warsaw, IN (US)

(*) Notice: Subject to any disclaimer, the term of this patent is extended or adjusted under 35 U.S.C. 154(b) by 147 days.

(21) Appl. No.: 16/293,382

(22) Filed: Mar. 5, 2019

(65) Prior Publication Data
US 2020/0281637 A1  Sep. 10, 2020

(51) Int. Cl.
| A61B 17/88 | (2006.01) |
| A61B 17/86 | (2006.01) |
| A61B 17/72 | (2006.01) |
| A61B 17/17 | (2006.01) |
| A61F 2/08 | (2006.01) |
| A61B 17/90 | (2006.01) |

(52) U.S. Cl.
CPC .......... *A61B 17/88* (2013.01); *A61B 17/1725* (2013.01); *A61B 17/7291* (2013.01); *A61B 17/86* (2013.01); *A61B 17/8875* (2013.01); *A61F 2/0805* (2013.01); *A61B 2017/90* (2013.01)

(58) Field of Classification Search
CPC .... A61F 2/0805; A61B 17/1725; A61B 17/88
See application file for complete search history.

(56) References Cited

U.S. PATENT DOCUMENTS

| 2,614,559 A | 10/1952 | Livingston |
| 4,016,874 A | 4/1977 | Maffei |

(Continued)

FOREIGN PATENT DOCUMENTS

| WO | 2006091460 A1 | 8/2006 |
| WO | 2007138062 A1 | 12/2007 |

(Continued)

OTHER PUBLICATIONS

International Search Report for PCT/US2012/022723 dated Jul. 6, 2012.

(Continued)

*Primary Examiner* — Christian A Sevilla
(74) *Attorney, Agent, or Firm* — Heslin Rothenberg Farley & Mesiti P.C.; Victor A. Cardona, Esq.

(57) ABSTRACT

An orthopedic instrument assembly for placing an implant into a bone has a targeting guide having an adjustable targeting arm, and a targeting aperture, where the targeting aperture defines a targeting axis through the targeting aperture. The orthopedic instrument assembly has a post having a longitudinal axis and the post connectable to the targeting guide. The post has a post aperture a post aperture center. The post aperture is aligned at a predefined angle relative to the longitudinal axis, where the post aperture defines a post aperture axis through the post aperture, the post aperture axis intersecting the longitudinal axis at the post aperture center. The adjustable targeting arm is for aligning the targeting axis with the post aperture center and thereby aligning the targeting aperture with the post aperture.

21 Claims, 23 Drawing Sheets

(56) References Cited

U.S. PATENT DOCUMENTS

| | | |
|---|---|---|
| 4,541,424 A | 9/1985 | Grosse |
| 4,622,959 A | 11/1986 | Marcus |
| 5,295,991 A | 3/1994 | Frigg |
| 5,411,504 A | 5/1995 | Vilas |
| 5,474,561 A | 12/1995 | Yao |
| 5,480,402 A | 1/1996 | Kim |
| 6,030,391 A | 2/2000 | Brainard et al. |
| 6,093,192 A | 7/2000 | Abel |
| 6,210,414 B1 | 4/2001 | Lin |
| 6,517,541 B1 | 2/2003 | Sesic |
| 6,579,293 B1 | 6/2003 | Chandran |
| 6,620,195 B2 | 9/2003 | Goble |
| 7,169,149 B1 | 1/2007 | Hajianpour |
| 7,179,259 B1 | 2/2007 | Gibbs |
| 7,311,710 B2 | 12/2007 | Zander |
| 7,713,291 B2 | 5/2010 | Vaughan |
| 8,034,056 B2 | 10/2011 | Fencl |
| 8,157,803 B1 | 4/2012 | Zirkle, Jr. |
| 8,187,281 B2 | 5/2012 | Cresina et al. |
| 8,257,361 B2 | 9/2012 | Ritchey |
| 8,303,589 B2 | 11/2012 | Tyber et al. |
| 8,313,487 B2 | 11/2012 | Tyber et al. |
| 8,328,806 B2 | 12/2012 | Tyber et al. |
| 8,343,199 B2 | 1/2013 | Tyber et al. |
| 8,486,071 B2 | 7/2013 | Jensen |
| 8,679,119 B2 | 3/2014 | Lopez-Oliva Munoz |
| 8,821,546 B2 | 9/2014 | Vaughan |
| 8,900,274 B2 | 12/2014 | Tyber et al. |
| 8,920,453 B2 | 12/2014 | Tyber et al. |
| 8,920,476 B2 | 12/2014 | Tyber et al. |
| D722,380 S | 2/2015 | Palmer |
| 9,017,329 B2 | 4/2015 | Tyber et al. |
| 9,044,282 B2 | 6/2015 | Tyber et al. |
| 9,107,709 B2 | 8/2015 | Wieland et al. |
| 9,289,220 B2 | 3/2016 | Wolfe et al. |
| 9,364,271 B2 | 6/2016 | Tyber et al. |
| 9,421,103 B2 | 8/2016 | Jeng et al. |
| 9,603,640 B2 | 3/2017 | Palmer et al. |
| 9,615,870 B2 | 4/2017 | Tyber et al. |
| 9,622,805 B2 | 4/2017 | Santrock et al. |
| 9,662,221 B2 | 5/2017 | Surma et al. |
| 9,814,474 B2 | 11/2017 | Montoya et al. |
| 9,877,752 B2 | 1/2018 | Tyber et al. |
| 9,907,562 B2 | 3/2018 | Dacosta et al. |
| 9,936,994 B2 | 4/2018 | Smith et al. |
| 9,936,995 B2 | 4/2018 | Dacosta et al. |
| 9,943,347 B2 | 4/2018 | Wayne et al. |
| 10,045,807 B2 | 8/2018 | Santrock et al. |
| 10,327,829 B2 | 6/2019 | Dacosta et al. |
| 10,335,220 B2 | 7/2019 | Smith et al. |
| 10,390,844 B2 | 8/2019 | Wieland et al. |
| 2003/0073999 A1 | 4/2003 | Putnam |
| 2003/0135216 A1 | 7/2003 | Sevrain |
| 2005/0055023 A1 | 3/2005 | Sohngen |
| 2005/0107791 A1 | 5/2005 | Manderson |
| 2005/0283154 A1 | 12/2005 | Orbay |
| 2006/0015123 A1 | 1/2006 | Fencl |
| 2006/0122600 A1 | 6/2006 | Cole |
| 2008/0077132 A1 | 3/2008 | Medoff |
| 2008/0147066 A1 | 6/2008 | Longsworth |
| 2009/0036931 A1 | 2/2009 | Pech et al. |
| 2009/0149861 A1 | 6/2009 | Brodsky |
| 2009/0157077 A1 | 6/2009 | Larsen |
| 2009/0299229 A1 | 11/2009 | Fencl |
| 2010/0036440 A1 | 2/2010 | Morris |
| 2010/0114315 A1 | 5/2010 | Manderson |
| 2010/0179550 A1* | 7/2010 | Schreiber ........... A61B 17/1725 606/62 |
| 2011/0125153 A1 | 5/2011 | Tyber et al. |
| 2011/0160728 A1 | 6/2011 | Blitz et al. |
| 2011/0230884 A1 | 9/2011 | Mantzaris et al. |
| 2011/0245885 A1 | 10/2011 | Powell |
| 2012/0095560 A1 | 4/2012 | Donner |
| 2012/0277745 A1 | 11/2012 | Lizee |
| 2012/0330313 A1 | 12/2012 | Grady |
| 2013/0030446 A1 | 1/2013 | Wayne |
| 2013/0245626 A1 | 9/2013 | Lavi |
| 2013/0325006 A1 | 12/2013 | Michelinie |
| 2014/0243827 A1 | 8/2014 | Boileau |
| 2015/0032168 A1 | 1/2015 | Orsak et al. |
| 2015/0173811 A1 | 6/2015 | Tyber et al. |
| 2015/0265323 A1 | 9/2015 | Sems |
| 2016/0354128 A1 | 12/2016 | Jeng et al. |
| 2017/0164989 A1 | 6/2017 | Weiner et al. |
| 2017/0216043 A1 | 8/2017 | Surma et al. |
| 2018/0161079 A1 | 6/2018 | Tyber et al. |
| 2018/0193039 A1 | 7/2018 | Dacosta et al. |
| 2018/0242987 A1 | 8/2018 | Lintula et al. |
| 2018/0242988 A1 | 8/2018 | Dacosta et al. |
| 2018/0280069 A1 | 10/2018 | Barmes et al. |
| 2018/0289379 A1 | 10/2018 | Dacosta et al. |
| 2018/0317992 A1 | 11/2018 | Santrock et al. |
| 2019/0117238 A1 | 4/2019 | Levitt |
| 2019/0125418 A1 | 5/2019 | Muller et al. |
| 2019/0274745 A1 | 9/2019 | Smith et al. |
| 2019/0307498 A1 | 10/2019 | Dacosta et al. |
| 2019/0328436 A1 | 10/2019 | Bays et al. |

FOREIGN PATENT DOCUMENTS

| | | |
|---|---|---|
| WO | 2010033702 A2 | 3/2010 |
| WO | 2018/157168 A1 | 8/2018 |
| WO | 2018/157170 A1 | 8/2018 |
| WO | 2018/183875 A1 | 10/2018 |
| WO | 2018/183884 A2 | 10/2018 |
| WO | 2018/202782 A2 | 11/2018 |
| WO | 2019/027821 A1 | 2/2019 |

OTHER PUBLICATIONS

International Search Report for PCT/US2012/022755 dated Jul. 6, 2012.

International Preliminary Report on Patentability for PCT Application No. PCT/US2012/022723, dated Aug. 8, 2013.

International Preliminary Report on Patentability for PCT Application No. PCT/US2012/022755, dated Aug. 8, 2013.

* cited by examiner

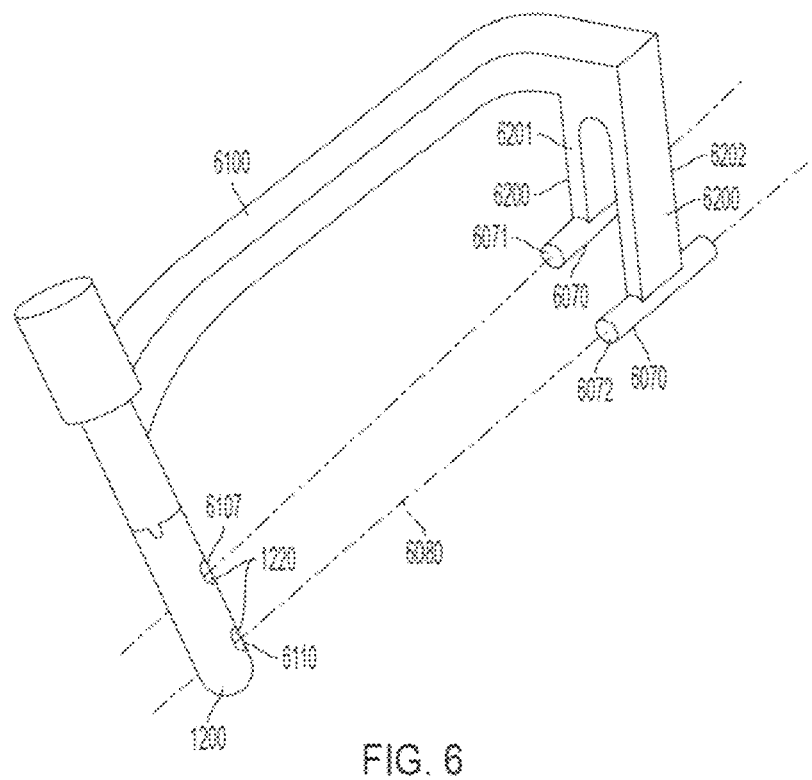
FIG. 6
FIG. 7
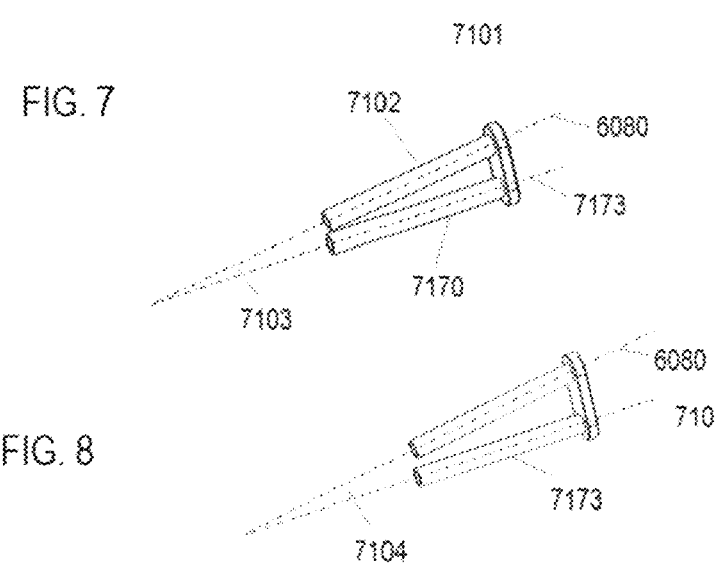
FIG. 8

BONE DEFECT REPAIR APPARATUS AND METHOD

CROSS-REFERENCE TO RELATED APPLICATIONS

This application is related to U.S. Pat. No. 9,603,640, Ser. No. 13/982,152, entitled "Lower Extremity Fusion Devices and Methods", filed on Jul. 26, 2013; U.S. Pat. No. 9,662,221, Ser. No. 13/982,124, entitled "Upper Extremity Fusion Devices and Methods", filed on Aug. 26, 2013; U.S. application Ser. No. 15/488,903, entitled "Upper Extremity Fusion Devices and Methods", filed on Apr. 17, 2017; and U.S. application Ser. No. 16/221,036 entitled "Bone Defect Repair Apparatus And Method", filed on Dec. 14, 2018; the entire disclosures of which are incorporated herein by reference.

BACKGROUND

Field of the Invention

This application relates generally to apparatuses, devices, and methods for joining bones and more particularly to apparatuses, devices, and methods providing flexible bone fastener connectivity.

Description of the Related Art

Hallux valgus is the medical term for a bunion. The first tarsal-metatarsal (TMT) joint is an important joint at the inner part of the middle of the foot. The two bones that meet to form this joint are the first metatarsal and medial cuneiform bones. When this joint has too much looseness or movement, the condition is known as hypermobility or instability. When this joint becomes hypermobile, the first metatarsal moves too much in one direction and the first toe compensates by moving too much in the other direction. When this happens, a bunion develops.

The Lapidus procedure is a type of fusion of the first TMT joint that decreases the movement of that joint and straightens out the first metatarsal and toe, so the Lapidus procedure treats bunions caused by first TMT joint hypermobility.

The goal of the Lapidus procedure is to surgically treat hallux valgus that is caused by first TMT joint hypermobility. An orthopedic foot and ankle surgeon realigns to a normal toe shape by placing the first metatarsal straight with the medial cuneiform bone and locking or fusing these two bones together. When the first TMT joint is fused, the first metatarsal will not move abnormally. This will allow the first toe to stay straight and prevent the bunion from coming back.

Hammertoe deformity, the most common deformity of the lesser toes, is a flexion deformity of the proximal interphalangeal (PIP) joint of the toe, with hyperextension of the metatarsophalangeal (MTP) and distal interphalangeal (DIP) joints. Progressive PIP joint flexion deformity typically leads to compensatory hyperextension of the MTP and DIP joints. This makes the PIP joint prominent dorsally. Pain occurs due to rubbing of the prominence against the patient's shoe. The deformity is flexible at first but usually becomes fixed over time. When the deformity is flexible, various procedures can be utilized that involve manipulation of the involved tendons. However, when the deformity is fixed, PIP fusion or joint replacement is often required. Implants available for fusion include the Digital Compression Screw (BioPro®, Port Huron Mich.), Smart Toe™ Intramedullary Memory Implant (Memometal Inc., Memphis Tenn.) and StayFuse™ Intramedullary Fusion Device (Tornier, Inc. Edina, Minn.). With these current implants, placement is critical because, when mounted, there is no adjustability in the angle of flexion between the two cut bones to be joined.

Current technology for repairing and fusing bones includes k-wire fixation, screws, plates and screws, and internal rods(posts) anchored with screws. Internal rod fixation has the advantage of being internal to the bone when compared to plate fixation. Plates are placed on the bone and can lead to soft tissue irritation. A disadvantage of internal rod fixation is that once the rod is placed in bone, the trajectory of the anchoring screws cannot be adjusted, leading sometimes to non-ideal screw starting locations, bone purchase, and trajectory. This may result in poor bone use, iatrogenic tissue damage, and interference with orthopedic hardware. Thus, a need exists for devices, systems, and methods for internal rod fixation that provide for screw trajectory adjustment and fastening.

SUMMARY

In one exemplary embodiment the present invention includes an orthopedic instrument assembly for placing an implant into a bone. The orthopedic instrument assembly has a targeting guide having a targeting aperture for alignment with a post aperture, and a post having a longitudinal axis. The post is connectable to the targeting guide such that the targeting guide and the post are rotatably moveable about the longitudinal axis with the post having the post aperture aligned at a predefined angle relative to the longitudinal axis. The orthopedic instrument assembly has a targeting guide offset for adjusting alignment of the targeting aperture, with the targeting guide offset having an insertion member, connectable to the targeting aperture, a guide adjustment member, the guide adjustment member having a guide adjustment aperture extending through the at least one guide adjustment member, and an adjustable offset axis through the guide adjustment member. The guide adjustment member defines the adjustable offset axis relative to the targeting aperture, for alignment with the post aperture.

In another exemplary embodiment the present invention includes an orthopedic instrument assembly for placing an implant into a bone. The orthopedic instrument assembly has a targeting guide, having a targeting aperture for alignment with a post aperture, and a post, having a longitudinal axis. The post is connectable to the targeting guide such that the targeting guide and the post are rotatably moveable about the longitudinal axis. The post further has the post aperture aligned at a predefined angle relative to the longitudinal axis and the post aperture has at least one internal engagement structure, configured for a plurality of alignments of a screw for engaging the post.

In another exemplary embodiment the present invention includes an orthopedic instrument assembly for placing an implant into a bone. The orthopedic instrument assembly has, a targeting guide having a targeting aperture for alignment with a post aperture, and a post, having a longitudinal axis. The post is connectable to the targeting guide such that the targeting guide and the post are rotatably moveable about the longitudinal axis. The post further has the post aperture aligned at a predefined angle relative to the longitudinal axis and the post aperture has at least one internal engagement structure configured for a plurality of alignments of a screw for engaging the post. The orthopedic instrument assembly has a targeting guide offset for adjusting alignment of the targeting aperture, the targeting guide offset having an insertion member connectable to the at least one targeting aperture, and a guide adjustment member, the guide adjustment member having a guide adjustment aperture extending through the at least one guide adjustment member and an adjustable offset axis through the guide adjustment member. The guide adjustment member defines the adjustable offset axis relative to the targeting aperture, for alignment with the post aperture.

A post for use with a targeting guide and configured to anchor into a bone. The post has a body having generally cylindrical shape and a longitudinal axis. The post further has a plurality of post apertures having a circumference, an unthreaded internal engagement structure, with the internal engagement structure having members extending radially inward from the circumference of the aperture. The post also has a screw having a primary axis, a threading on a leading end thereof, and the threading having a pitch. The post further has a post fastener connectable to a targeting guide such that the targeting guide and the post are rotatably moveable about the longitudinal axis.

In another exemplary embodiment, an orthopedic instrument assembly for placing an implant into a bone having a targeting guide having an adjustable targeting arm, and a targeting aperture, where the targeting aperture defines a targeting axis through the targeting aperture. The orthopedic instrument assembly further has a post having a longitudinal axis and the post connectable to the targeting guide. The post has a post aperture and a post aperture center. The post aperture is aligned at a predefined angle relative to the longitudinal axis, where the post aperture defines a post aperture axis through the post aperture, the post aperture axis intersecting the longitudinal axis at the post aperture center. The adjustable targeting arm is for aligning the targeting axis with the post aperture center and thereby aligning the targeting aperture with the post aperture.

In another exemplary embodiment, an orthopedic instrument assembly for placing an implant into a bone having a targeting guide having an adjustable targeting arm, and a targeting aperture, where the targeting aperture defines a targeting axis through the targeting aperture. The orthopedic instrument assembly further has a post having a longitudinal axis and the post connectable to the targeting guide. The post has a post aperture and a post aperture center. The post aperture defines a post aperture axis through the post aperture, the post aperture axis intersecting the longitudinal axis at the post aperture center. The post aperture has at least one internal engagement structure, said internal engagement structure configured for a plurality of alignments of a screw for engaging the post. The adjustable targeting arm is for aligning the targeting axis with the post aperture center and aligning the targeting aperture with the post aperture.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

FIG. 6 is a perspective view of an alternate embodiment of an assembled targeting guide, implant post, and implant post fastener with the post engaged with the fastener.

FIG. 7 is a perspective view of a targeting guide offset for a small offset angle.

FIG. 8 is a perspective view of a targeting guide offset for a large offset angle.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for cutting tools for orthopedic surgery involving a foot or lower extremities. However, those possessing an ordinary level of skill in the relevant art will appreciate that other extremities, joints, and parts of the musculoskeletal system are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to any orthopedic surgery, such as on the hand as well as other upper and lower extremities and may be implemented in other treatments sites that have similar anatomical considerations.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
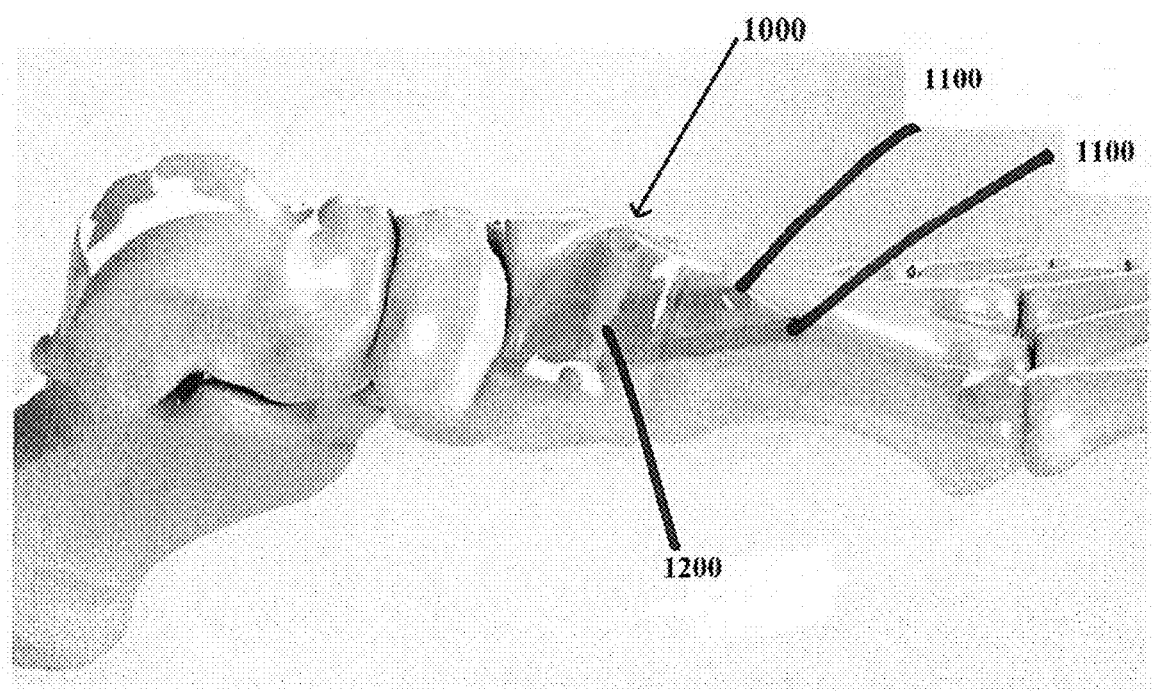
FIG. 1 is a perspective view of an implant inserted into a bone for use with an aspect of the invention.

As depicted in FIG. 1, an orthopedic implant 1000 is implanted into a human foot to correct a deformity. As will be described below, the present invention comprises surgical instruments and methods for properly placing implant 1000 into a medial cuneiform of the human foot in a manner that maximizes the amount of bone surrounding the implant by targeting the major axis of the cross section of the bone.

Figure 2:
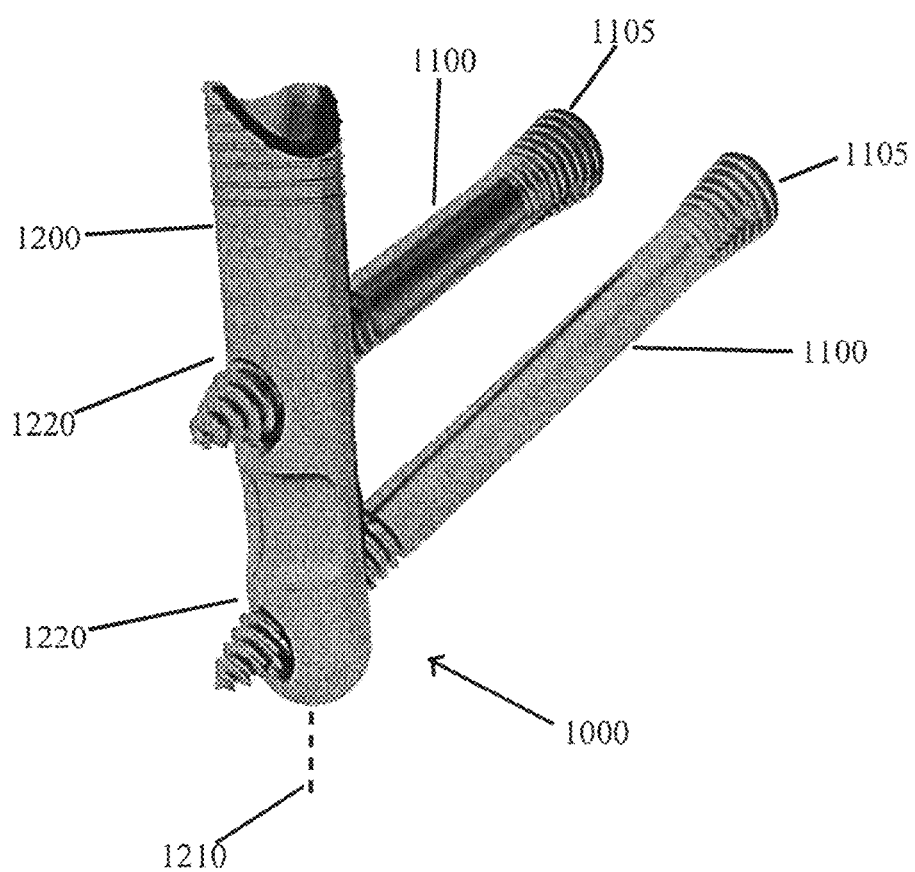
FIG. 2 is a perspective view of an implant for use with an aspect of the present invention.

Referring now to FIGS. 1 and 2, implant 1000 includes screws 1100. It is common that two or more screws 1100 are used with an implant 1000, as shown in FIG. 2, however a single screw may also be used (see FIG. 14). An embodiment of screws 1100 may be solid shafted as shown in FIG. 2. "Solid shafted" means that the portion of the screw that crosses the joint is not threaded and is at the major diameter of the distal screw thread. Screws 1100 cross the medial cuneiform/first metatarsal joint and lock into a post 1200. Locking screws 1100 into post 1200 requires seating the screws 1100 to internal threading or internal engagement structures (see FIGS. 11-17) within apertures 1220 in post 1200, such that the screws 1100 reach an end of potential advancement. In such a locked state, screws 1100 cannot move (translate or rotate) with respect to post 1200 or each other. Preferably, post 1200 has a diameter of 1.5 to 2.5 times a diameter of screws 1100. Heads 1105 of the screws 1100 are substantially tapered, "headless screws," allowing them to be seated further into bone than headed screws.

Figure 3:
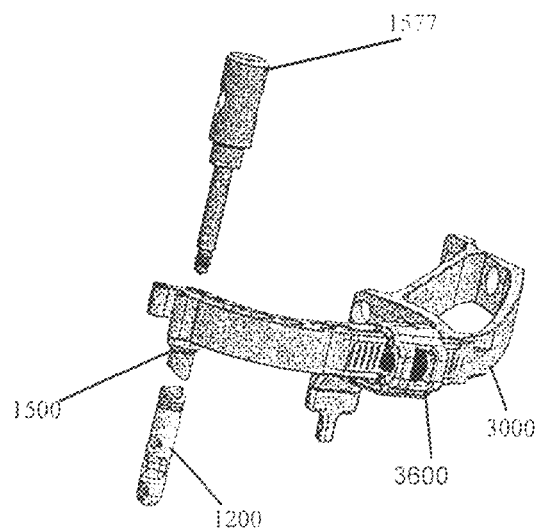
FIG. 3 is a disassembled perspective view of a targeting guide and post in accordance with the present invention.

Referring again to FIG. 2, implant post 1200 of implant 1000 comprises a substantially cylindrical shape having a longitudinal axis 1210 and post apertures 1220 with internal threading or internal engagement structures (see FIGS. 11-17), at predefined angles relative to longitudinal axis 1210 of post 1200. Post 1200 is configured to be releasably connected (eliminating rotation and translation with respect to) to a targeting guide 3000 (FIG. 3). Post 1200 connects to targeting guide 3000 at post support member 1500 by using a post fastener 1577. Targeting guide 3000 directs instrumentation to the post apertures 1220, with post apertures 1220 having internal threading or internal engagement structures (see FIGS. 11-17). The post aperture 1220 may be a hole or bore that may partially or completely extend through post 1200. The post 1200 may also be configured to receive a post plug to prevent bone growth into connection threads of the post (i.e., to allow easy removal). Post 1200 normally has at least one post aperture 1220. It is possible to have more than six post apertures 1220 but there are commonly six or less.

Figures 4, 5:
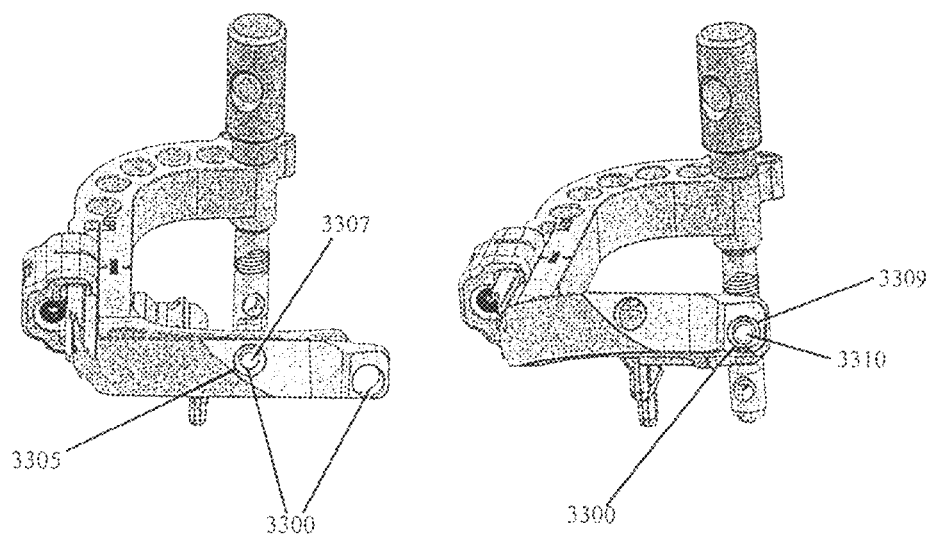
FIG. 4 depicts a rear perspective view of an assembled targeting guide, an implant post, and an implant post fastener of FIG. 3, with the post engaged with the fastener.
FIG. 5 depicts a rear perspective view of a targeting guide, implant post, and implant post fastener of FIG. 4 with a targeting aperture aligned with a post aperture.

Referring to FIGS. 3-5, targeting guide 3000 is preferably pre-assembled to implant 1000. The built-in compression-distraction fixture 3600 allows simplified joint preparation and pre-compression of the joint prior to placement of implant 1000. Targeting guide 3000 is preferably positioned substantially medial and dorsal to the bones being fused thereby reducing interference with X-ray imaging during procedure.

Referring generally to FIGS. 2-5, post 1200 and targeting guide 3000, when assembled, are rotatable around longitudinal axis 1210 (FIG. 2) of post 1200 when post 1200 is inserted in a bone to optimize a trajectory and a start location of implanted screws 1100 with respect to the bone. Post 1200 is removably attached to targeting guide 3000 at post support member 1500 by post fastener 1577.

Implant post 1200 may be assembled to targeting guide 3000 at post support member 1500 by threading post fastener 1577 into implant post 1200, with targeting guide 3000 positioned between.

Targeting apertures 3300 may be located as holes in targeting guide 3000, alignment can be visualized to ensure proper assembly and left/right foot selection. A medial hole 3305 of targeting apertures 3300 of the targeting guide may align with a plantar post aperture 3307 in post 1200 as depicted in FIG. 4. A lateral hole 3309 of targeting apertures 3300 of the targeting guide aligns with a dorsal post aperture 3310 of the post as depicted in FIG. 5. A surgeon may then perform soft tissue releases to ensure full mobility of a first metatarsal to a desired correction position and makes a dorsal incision over a tarsometatarsal joint.

The post may have one or more post apertures and accordingly, targeting guide 3000 will have at least a corresponding number of targeting apertures 3300.

Referring to FIG. 6 an alternate embodiment of a targeting guide 6100, showing an alternate embodiment of a targeting aperture 6070 connected to a leg 6200 extending below the targeting guide 6100. Targeting apertures 6070 are an embodiment of targeting apertures 3300 (see FIGS. 4, 5, 20, and 21). There may be only one leg 6200 or there may be more than one (e.g. a first leg 6201 and a second leg 6202). There may be also be a combination of targeting apertures 6070 and targeting apertures as holes 3300 (See FIGS. 4 and 5) in another embodiment of a targeting guide (not shown). A second targeting aperture 6072 of targeting apertures 6070 of the targeting guide 6100 aligns with a dorsal post aperture 6107 in post 1200. A first targeting aperture 6071 of targeting apertures 6070 of targeting guide 6100 may align with a plantar post aperture 6110 of post 1200. While targeting aperture 6070 is shown as a cylindrical structure, it is not necessary that it be cylindrical. Targeting aperture 6070 may include a single aperture in leg 6200, a cylinder, a double ring where the two rings are separated by a distance between them, or any targeting structure or sighting structure which facilitates targeting a point removed from targeting aperture 6070.

Referring to FIGS. 7-8, a targeting guide offset 7101 is shown with an insertion member 7102 and a guide adjustment member 7170, connected with a crosspiece 7105. Insertion member 7102 may be tubular or cylindrical, being of a size and shape to securely fit into targeting aperture 6070 (FIG. 6). Guide adjustment member 7170 has an aperture extending through guide adjustment member 7170. Crosspiece 7105 is shown as elliptical in shape, however crosspiece 7105 may be of any shape. Crosspiece 7105 may have the guide adjustment member 7170 going through the crosspiece 7105 or have an aperture aligned with guide adjustment member 7170 aperture, or it may just connect guide adjustment member 7105 and insertion member 7102.

Referring to FIGS. 6-8, targeting guide offsets 7101 may be used to adjust the alignment between targeting apertures 6070 and post apertures 1220. A targeting aperture axis 6080 is intended to align with a central axis of a post aperture (e.g. 9015, 9005, and 9006 in FIG. 16), however that is not always possible or desirable. There may also be situations where a positional refinement or angular refinement or an offset may be required because of a bone or hardware obstruction, or to maximize the best available bone. A small amount of positional refinement may be required to better aim and position a drill bit or insert a screw. Targeting guide offset 7101 may be used to adjust the angle of targeting aperture axis 6080. Targeting guide offset 7101 includes insertion member 7102 and guide adjustment member 7170.

Insertion member 7102 may be inserted into the targeting aperture 6070. Guide adjustment member 7170 is shown offset from the targeting aperture axis at a predetermined angle so that offset axis 7173 forms an angle with targeting aperture axis 6080 at or near post aperture 1220. Guide adjustment member 7170 has offset axis 7173, with common offsets of 4 degrees 7103 or 8 degrees 7104 from targeting aperture axis 6080 being formed. Other offset angles may also be used with most being application dependent. It is most common that guide adjustment member 7170 is offset from the targeting aperture axis at a predetermined angle. However, other embodiments may have guide adjustment member 7170 which may be movable about its connection to crosspiece 7105.

In FIGS. 7-8, a targeting guide offset 7101 is shown providing an angled offset. There may be an embodiment with a targeting guide offset with guide adjustment member 7170 having an offset axis 7173 that is parallel to targeting aperture axis 6080 and offset by distance from the targeting aperture.

Figure 9:
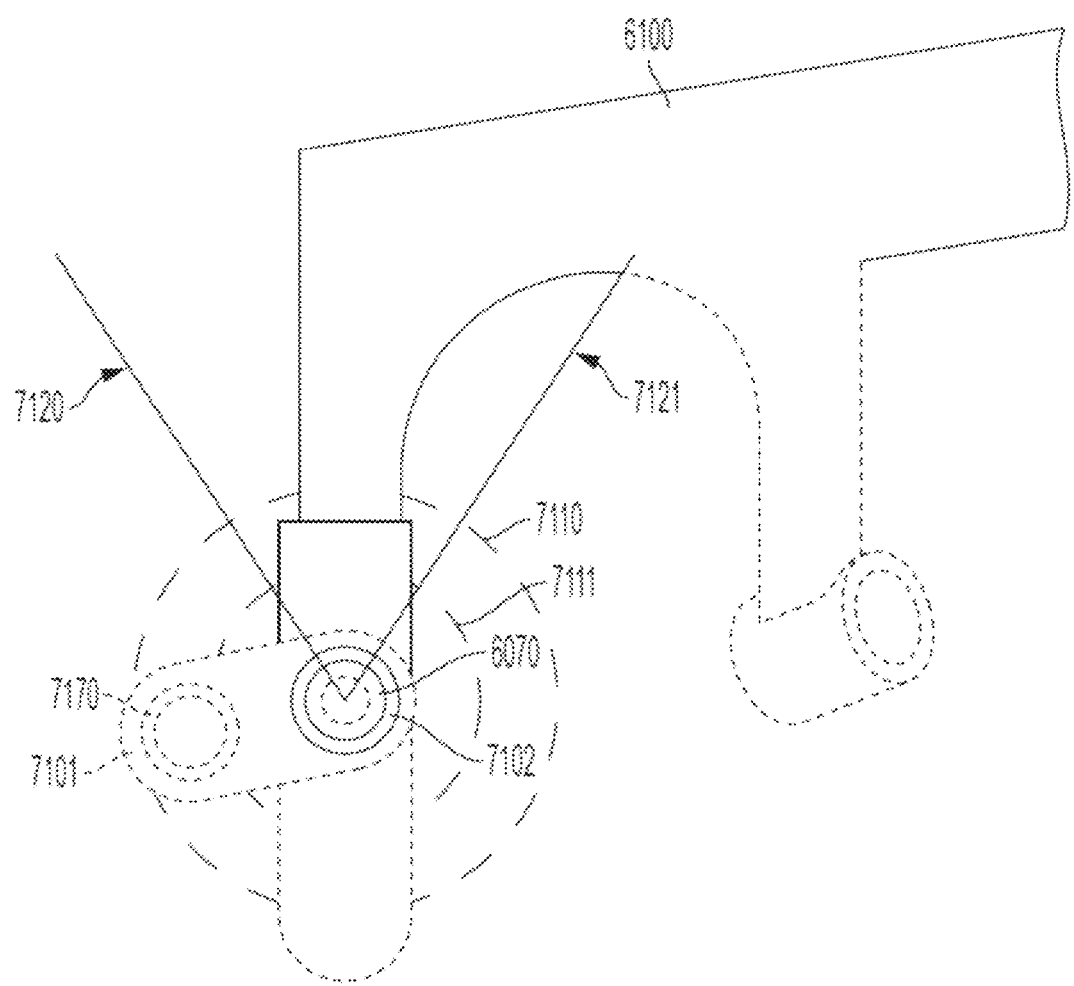
FIG. 9 depicts a rear view of the targeting guide offset of FIG. 7 connected to the targeting aperture of FIG. 6 and rotating in an arc about the targeting aperture.

Referring to FIG. 9 targeting guide offset 7101 is shown connected to targeting guide 6100. Insertion member 7102 being inserted into targeting aperture 6070 (see FIG. 6), guide adjustment member 7170 may rotate in an arc between positions 7120 and 7121. Rotation is about insertion member 7102 and positions 7120 and 7121 are offered as rotational endpoint reference positions in this embodiment. However, there may be embodiments that allow a more limited arc or embodiments that cover full 360 degree or more rotation in clockwise and anti-clockwise directions. Offset guide angles 7103 and 7104 (FIGS. 7-8) provide for target rings 7110 and 7111 respectively.

Insertion member 7102 should be sized to connect securely to targeting aperture 6070 so that it is not easily removable and so there is no wobble, free play, or lateral movement within the targeting aperture. The insertion member 7102 connection to targeting aperture 6070 may be frictional, to inhibit easy removal or free play. Guide adjustment member 7170 rotates freely about the insertion member.

Rotation is about insertion member 7102. Insertion member 7102 aligns or mostly aligns with targeting aperture axis 6080 in this embodiment. However, there may be embodiments where alignment between insertion member 7102 and targeting aperture axis 6080 is not desirable.

To maintain position once a desired offset position or alignment is obtained, either friction or a locking mechanism, such as a set screw, are used.

Figure 10:
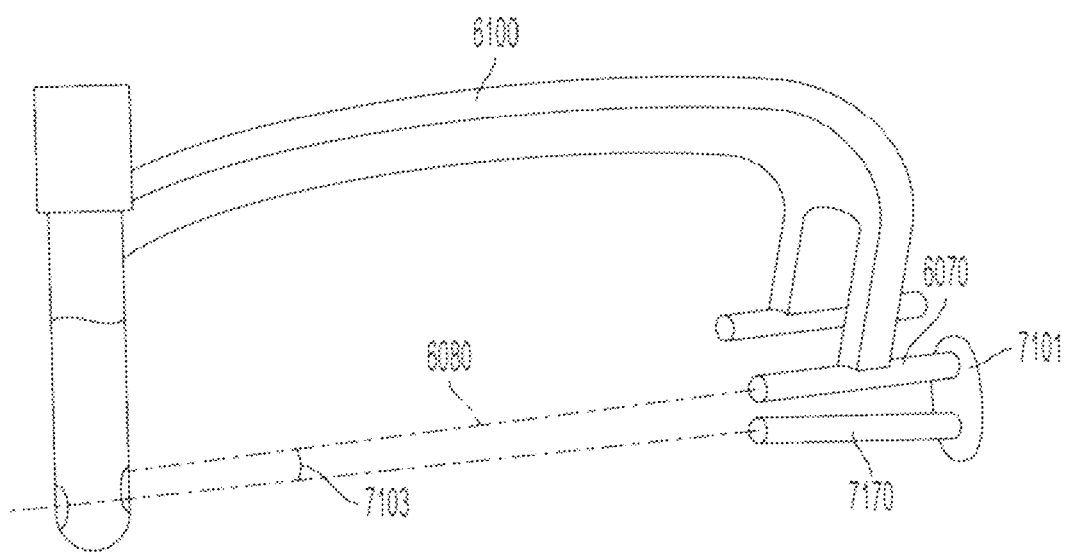
FIG. 10 depicts a side view of the targeting guide of FIG. 6 with targeting guide offset member of FIG. 8 connected to the targeting aperture of FIG. 6, and including an adjustable offset angle.

Referring to FIG. 10 targeting guide offset 7101 is shown connected to targeting guide 6100, with guide adjustment member 7170 providing an offset angle 7130.

Figure 11:
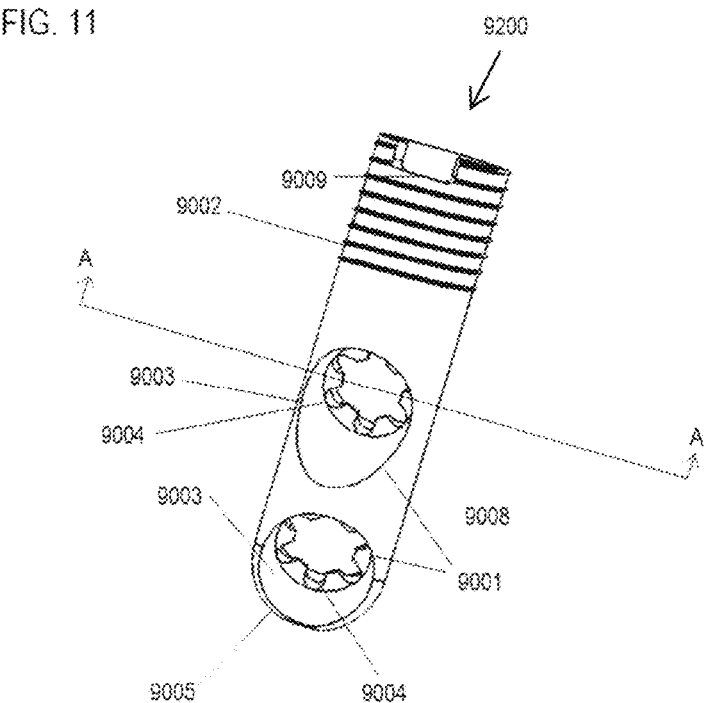
FIG. 11 is a perspective view of an implant post with implant apertures having screw guides.

Referring to FIG. 11 an embodiment of a post 9200 has a body 9008, at least one area with threading 9002, post apertures 9001, with the apertures having tapered wall 9003 extending from the opening, and each aperture having internal engagement structures 9004. The post 9200 may have one or more post apertures 9001. Post 1200 may have embodiments with internal engagement structures but no tapered wall or there may be other embodiments with tapered walls but no internal engagement structures beyond screw threading. There may still be other embodiments where there may multiple tapered walls or areas where the angle of the tapering differs. Post 9200 is shown with a recess 9009. Recess 9009 may be present in some embodiments to aid in connection and positioning with certain embodiments of a targeting guide (see FIG. 32). Recess 9009 may also be present in embodiments of post 1200 (see FIGS. 2 and 3). Post 9200 normally has at least one post aperture 9001. It is possible to have more than six post apertures 9001 but there are commonly six or less.

Figure 12:
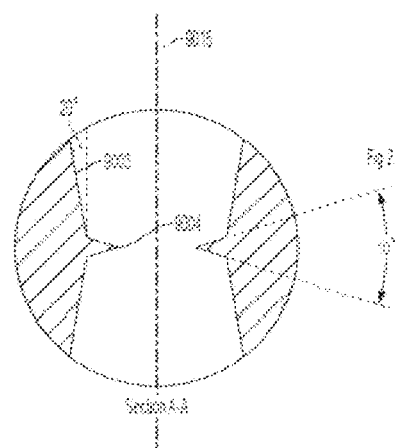
FIG. 12 depicts a cross sectional view of an implant aperture of FIG. 11 with screw guides, and engagement members.
Figure 13:
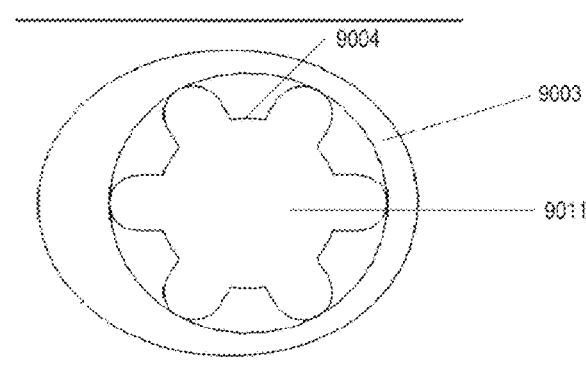
FIG. 13 depicts a close-up view of the implant aperture of FIG. 11.
Figure 14:
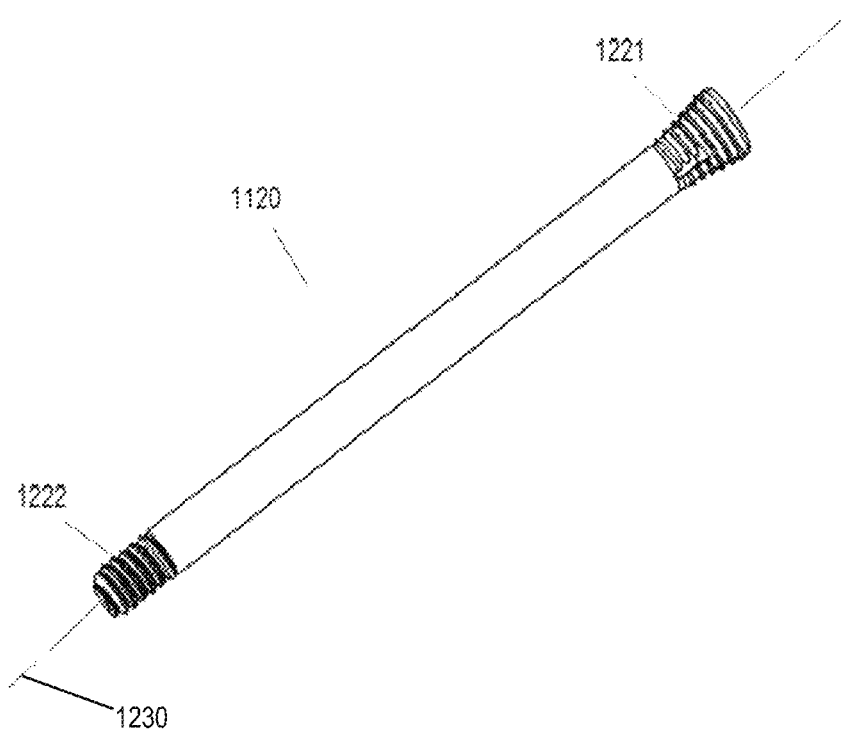
FIG. 14 depicts a perspective view of an implant screw with two threaded sections.
Figure 14A:
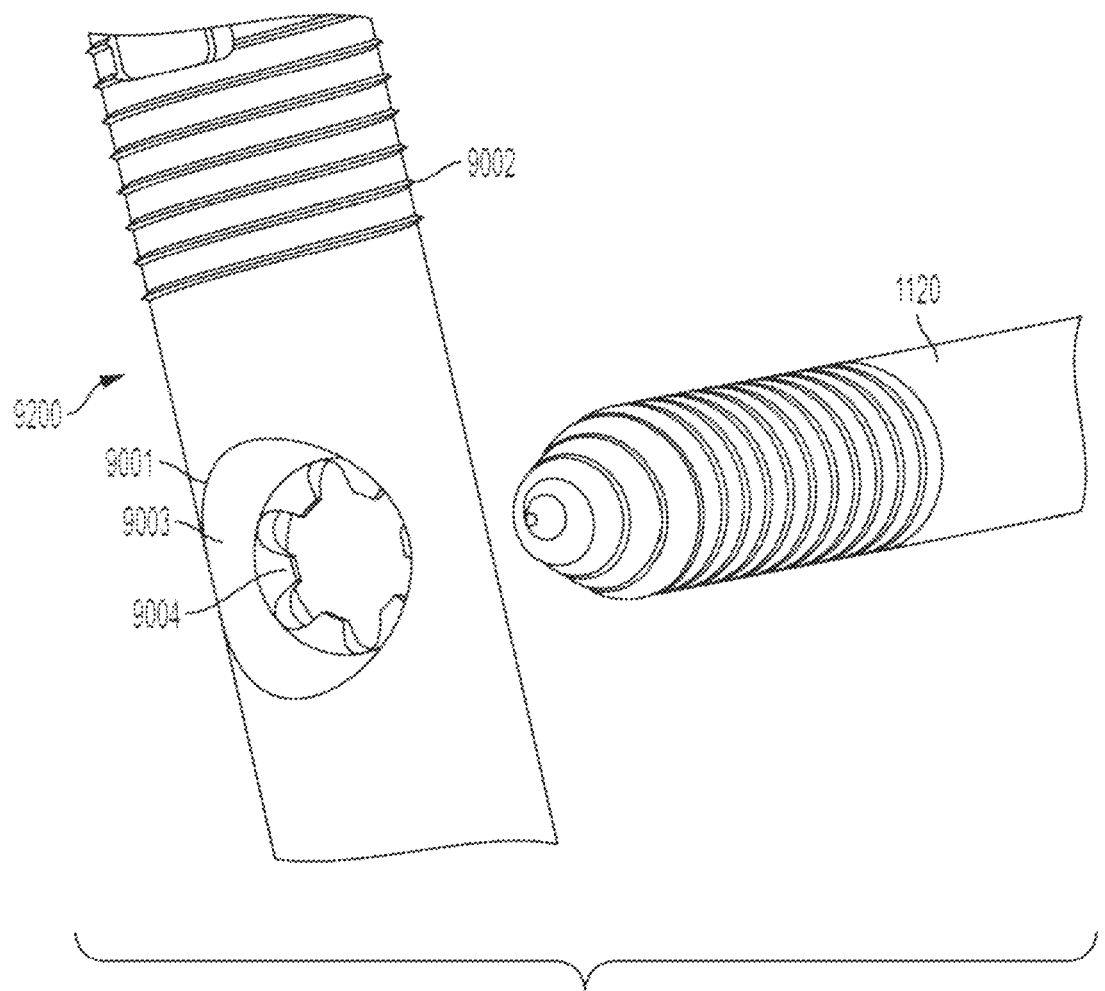
FIG. 14A is a closeup of the implant aperture of FIG. 11, with screw guides and engagement members in relation to a screw.

Referring generally to FIGS. 12-14, a horizontal cross-section of an embodiment of post aperture 9001 is shown, with a configuration to engage or nearly engage or partially engage with a threaded lead portion 1222 of screw 1120. Bone screw 1120 is an example of an individual screw of screws 1100. Bone screw 1120 has threaded lead portion 1222, which may have a cut or series of cuts for engagement with the internal engagement structure 9004 and for cutting thread or advancing screw 1120 into the bone or post 9200. Bone screw 1120 may also have a threaded rear portion 1221.

Referring to FIGS. 12-13, internal engagement structure 9004 is shown as a plurality of members extending radially inward from the circumference of the aperture and positioned radially about the circumference so that adjacent members may be in contact with each other at the aperture circumference. The internal engagement structures 9004 may extend radially inward in a plane perpendicular to the circumference of the aperture. The internal engagement members in FIG. 12 are shown connected to an aperture wall, the member extending at an angle of 10 degrees to a tapered end 9007. The individual internal engagement members may be angled to suit the application or the internal engagement members may be flat. The internal engagement structure may be unthreaded but it is for engagement with threading 1222 of a bone screw 1120.

Referring to FIGS. 12-14, post aperture thread engagement structures 9004 may be one or more structures positioned and having a height to engage or nearly engage the minor diameter of bone screw 1120; may be configured to match the pitch of bone screw 1120; may be of a height configured to primarily engage some or all of the aspects at the major diameter of the thread of bone screw 1120; may have one or more compliant planar members to match or nearly match the thread of threaded lead portion 1222, or somewhere in between; or combinations thereof. The compliant planar members engage with the thread of threaded lead portion 1222 of the bone screw 1120, moving the threaded lead portion 1222 with respect to the primary axis 1230 of the screw so that screw 1120 threads into post 1200. The planar members may be resilient or elastically deformable in certain other embodiments. To aid in moving the thread with respect to the primary axis 1230, the compliant planar members may move in different directions (e.g. the planar members in the dorsal section of post aperture 9001 may bend in the axial direction of screw motion and the planar members in the plantar sections of post aperture 9001 may bend in the axial direction against screw motion).

Further referring to FIG. 12-14 the post aperture 9001 may have an angled or tapered inner surface 9003 to further aid in guiding bone screw 1120 towards internal engagement structures 9004. The internal thread engagement structures 9004 may have a sharp or blunt cross section. The combination of angled or tapered walls 9003 and internal thread engagement structures 9004 provide for varied engagement angles with the bone screw 1120. Permissible angles of approach relative to the post aperture axis 9015 are shown between and including 0 to 20 degrees in this embodiment. The angle of the approach may have slight variations, but it is most common that approaches will be from 0 to 20 degrees relative to the post aperture axis 9015.

Figure 15:
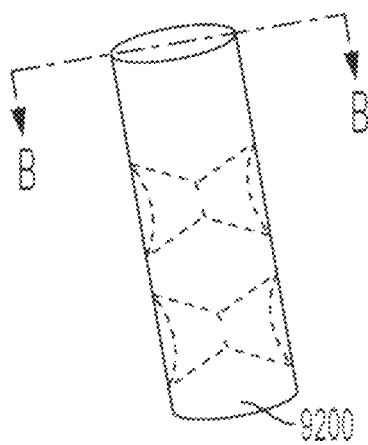
FIG. 15 depicts a side perspective view of the implant post of FIG. 11 indicating a vertical cross sectional cut.
Figure 16:
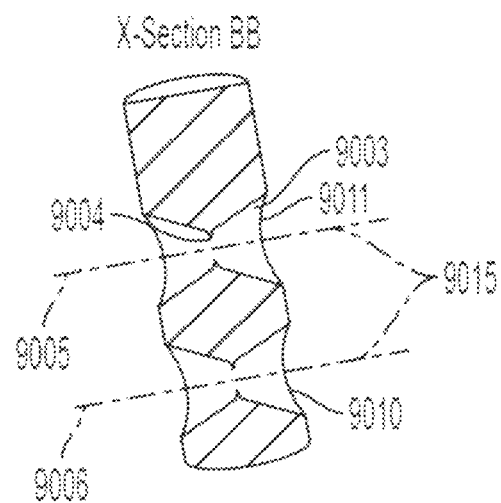
FIG. 16 depicts a vertical cross sectional cut of the implant post of FIG. 15.

Referring to FIGS. 15-16, a cross section of an implant post 9200 showing post apertures 9001, with tapered walls 9003 extending from the opening, thread engagement structures 9004, and post aperture axes 9015. Shown are post 9200 with a dorsal aperture 9011 and a plantar aperture 9010 and including a dorsal axis 9005 and a plantar axis 9006.

Figure 17:
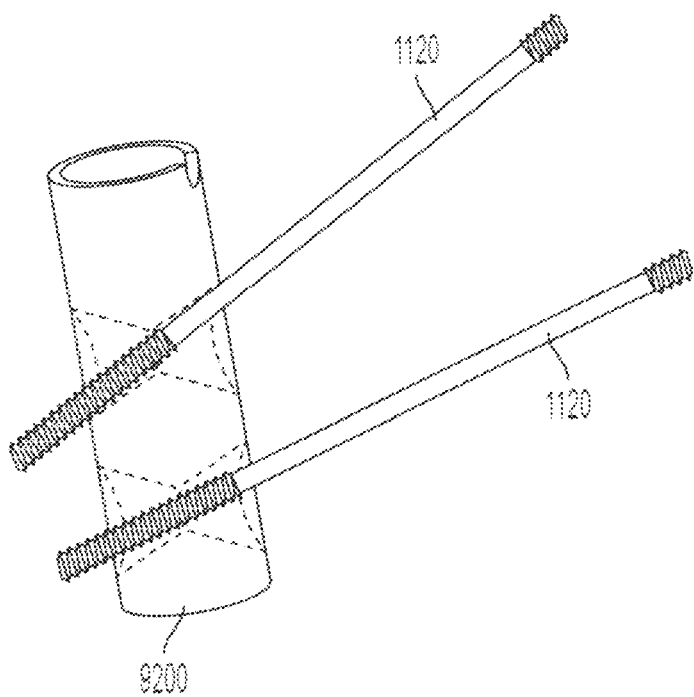
FIG. 17 depicts a cutaway view of the implant of FIG. 11 with a post having screw connection guides.

Illustrated in FIG. 17 is a cutaway view of a post 9200 with engaged screws 1120 shown.

The embodiment depicted in FIGS. 6-9 refers to use with post 1200, however it may also be used with post 9200 as depicted in FIGS. 11-13 and 14A-17.

Figure 18:
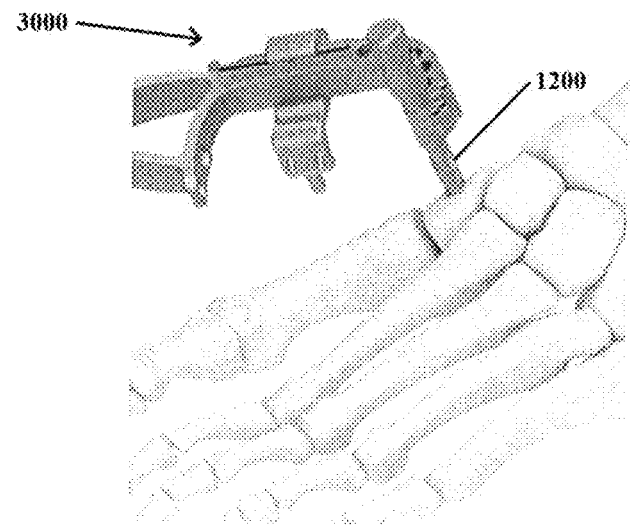
FIG. 18 depicts a perspective view of the targeting guide, implant post, and implant post fastener of FIG. 3 with the post received in a reamed hole in a bone.
Figure 19:
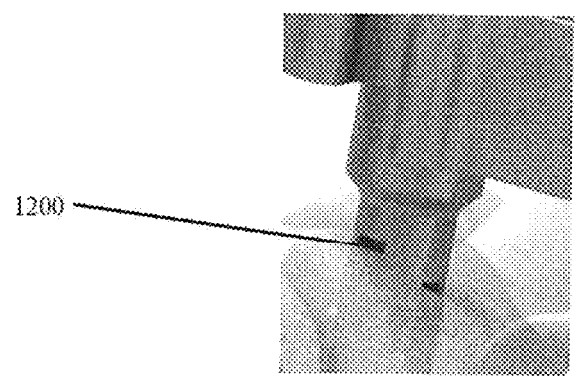
FIG. 19 depicts a close-up view of the post of FIG. 3 received in the bone.

As illustrated in FIG. 18-19, post 1200 and targeting guide 3000 assembly are shown connected to the medial cuneiform bone. The surgeon then may fully seats post 1200 into the bone ensuring targeting guide 3000 depth lines are at or just below bone surface, as further described in related U.S. application Ser. No. 16/221,036.

In FIGS. 18-21, targeting guide 3000 is depicted with post 1200. Alternative embodiments may use post 9200, instead of post 1200, with targeting guide 3000.

Figure 20:
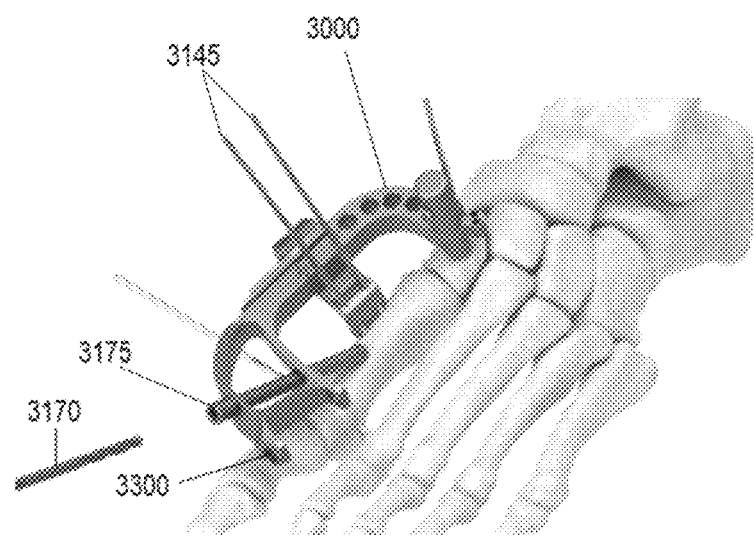
FIG. 20 depicts a top view of the targeting guide of FIG. 3, connected to a bone, with a bushing and a drill bit.
Figure 21:
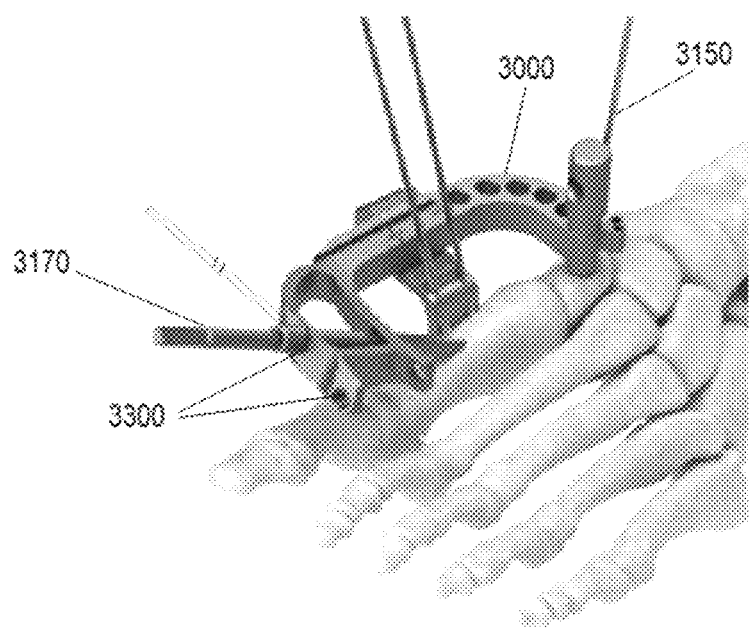
FIG. 21 depicts a top perspective view of the targeting guide and drill bit of FIG. 3 with the drill bit engaged with the targeting guide.

As depicted in FIGS. 20-21, once desired correction of the metatarsal is achieved and secured in compression, the surgeon places a bushing 3175 into medial hole 3305 in the targeting guide 3000. The bushing may be chosen to be the longest bushing that will fully seat against guide 3000 without touching the metatarsal. A drill bit 3170 (e.g., a 3.6 mm drill bit) is introduced into bushing 3175 and fully seats drill bit 3170 against bushing 3175 (up to a step on the drill bit) to ensure that the drill creates a continuous tunnel of an appropriate length to post 1200.

Where targeting guide offset 7101 is used, targeting guide offset 7101 may be locked into place, once desired metatarsal correction is achieved, and the metatarsal is secured in compression. Locking prevents targeting guide offset 7101 from further rotation and maintains positional alignment. The surgeon may place a bushing 3175 into medial hole 3305 in guide adjustment member 7170. The bushing may be chosen to be the longest bushing that will fully seat in guide adjustment member 7170 without touching the metatarsal. A drill bit 3170 (e.g., a 3.6 mm drill bit) is introduced into bushing 3175 and fully seats drill bit 3170 against bushing 3175 (up to a step on the drill bit) to ensure that the drill creates a continuous tunnel of an appropriate length to post 1200.

Figure 22:
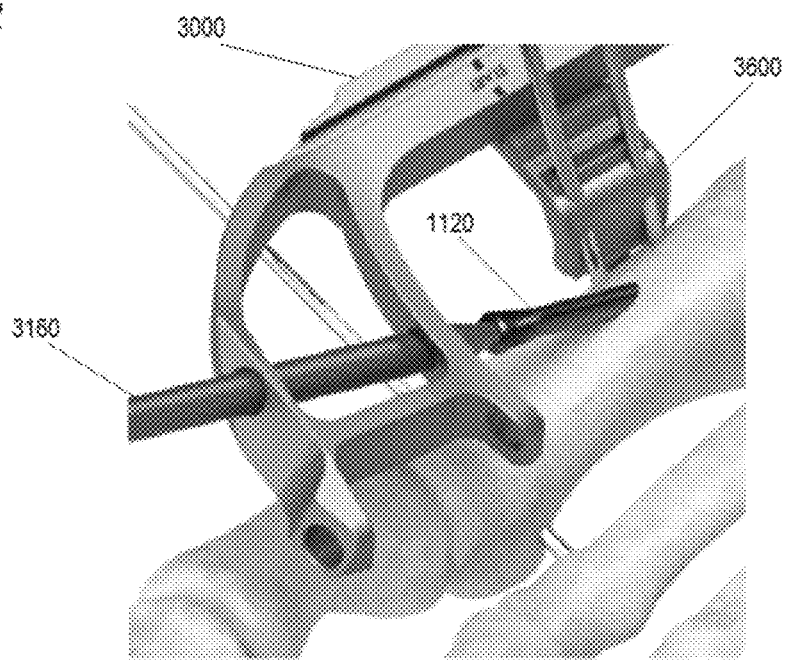
FIG. 22 depicts a closeup view of a section of the targeting guide of FIG. 3 with a screw inserted into a tunnel in the bone.
Figure 23:
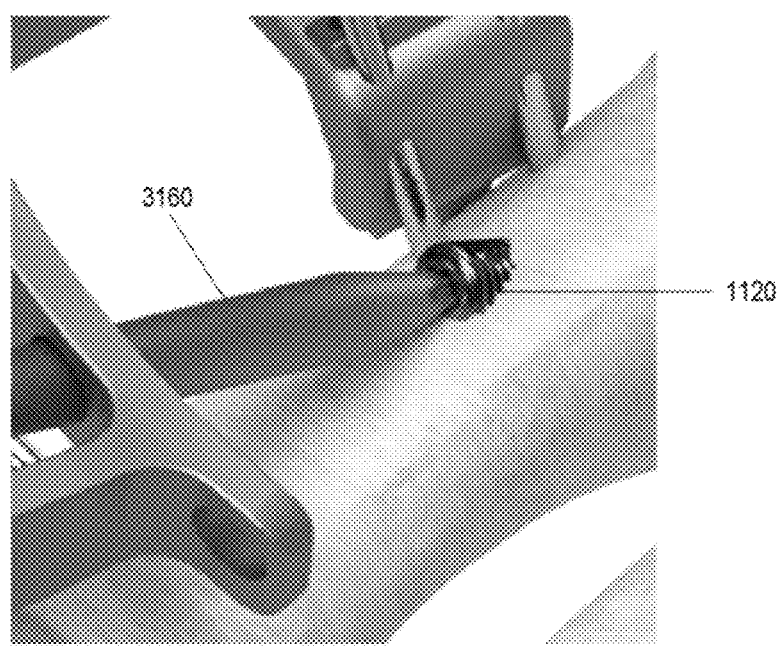
FIG. 23 depicts a closeup of a section of the targeting guide and screw of FIG. 3 with the screw advanced into the bone.

As shown in FIGS. 22-23, once a hole has been drilled and the depth measured an appropriately sized screw 1120 is inserted through the drilled tunnel until it reaches post 9200.

Bone screw 1120 may be driven by a screwdriver operated by a surgeon. Such a screwdriver may be configured with an alignment feature which includes a cylindrical feature at the tip of the driver, smaller than the feature that generates torque, that inserts into a cylindrical hole feature at the bottom of the bone screw's 1120 drive feature (not marked). This alignment feature is important to ensure that the axis of the screw 1230 and the axis of the driver (not shown) are collinear. This prevents bone screw 1120 from deviating from the drilled tunnel (in soft bone) and missing the post aperture (not shown). Bone screw 1120 is configured to be minimally retained with the driver, such that it need not be held to the driver during insertion (i.e., so it doesn't fall off of the driver).

As depicted in FIGS. 3 and 20-23, targeting guide 3000 includes compression-distraction fixture 3600. Distraction fixture 3600 may be used to anchor targeting guide 3000 (see FIG. 20) to the metatarsal and to stabilize the corrected metatarsal position (i.e. the position after movement) by placing k-wires 3145 into the bone. Targeting guide 3000 may also rest against the metatarsal, aiding in positioning the targeting guide 3000.

Figure 24:
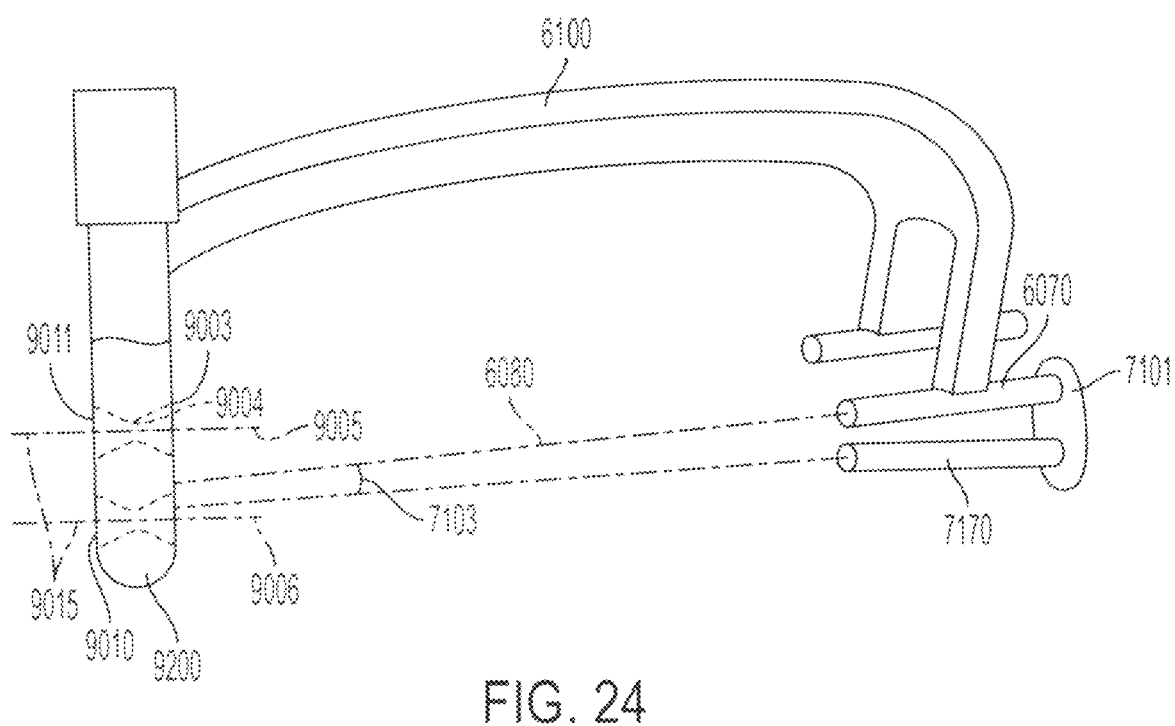
FIG. 24 depicts a side view of the targeting guide with the targeting guide offset of FIG. 10, inserted into a targeting aperture and adjusting the angle of the post aperture of the post of FIG. 11.

Depicted in FIG. 24 is targeting guide 6100 with targeting guide offset 7101 connected to a targeting aperture 6070. The targeting aperture is aligned with a plantar post aperture and guide adjustment member 7170, is also aligned with the plantar post aperture. Targeting aperture axis 6080, of the guide adjustment member, crosses a central axis of the plantar post aperture (e.g. 9010 or 6110). The post is shown in a vertical cross-sectional view with tapered entrances and engagement structures visible.

Figure 25:
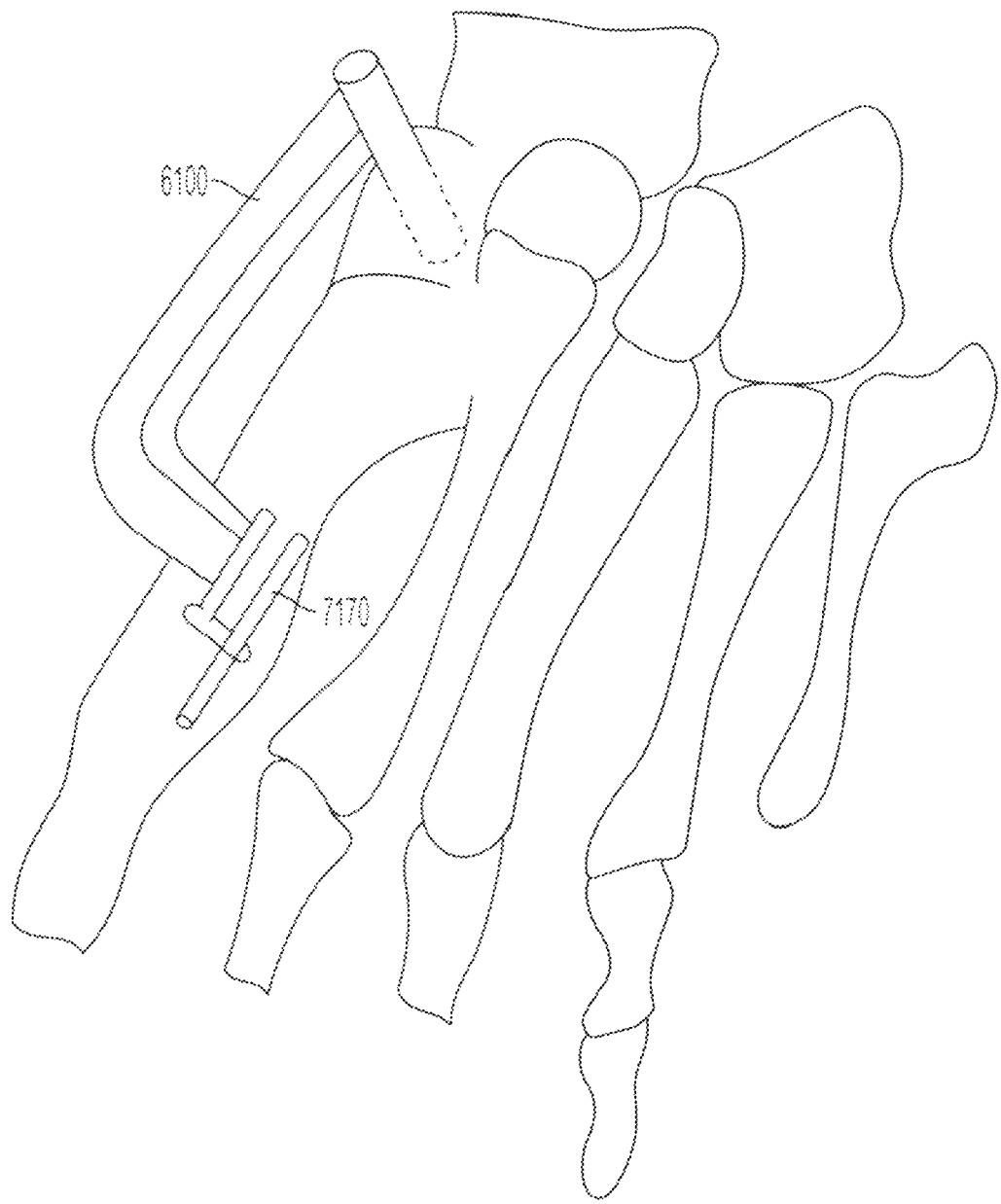
FIG. 25 depicts a perspective view of the targeting guide with the targeting guide offset of FIG. 10, inserted into a targeting aperture, with an implant post connected to a medial cuneiform bone.

Depicted in FIG. 25 is targeting guide 6100 connected to a medial cuneiform bone by a post implant and showing a drill-bit being inserted through a bushing connected to guide adjustment member 7170, into metatarsal bone.

Figure 26:
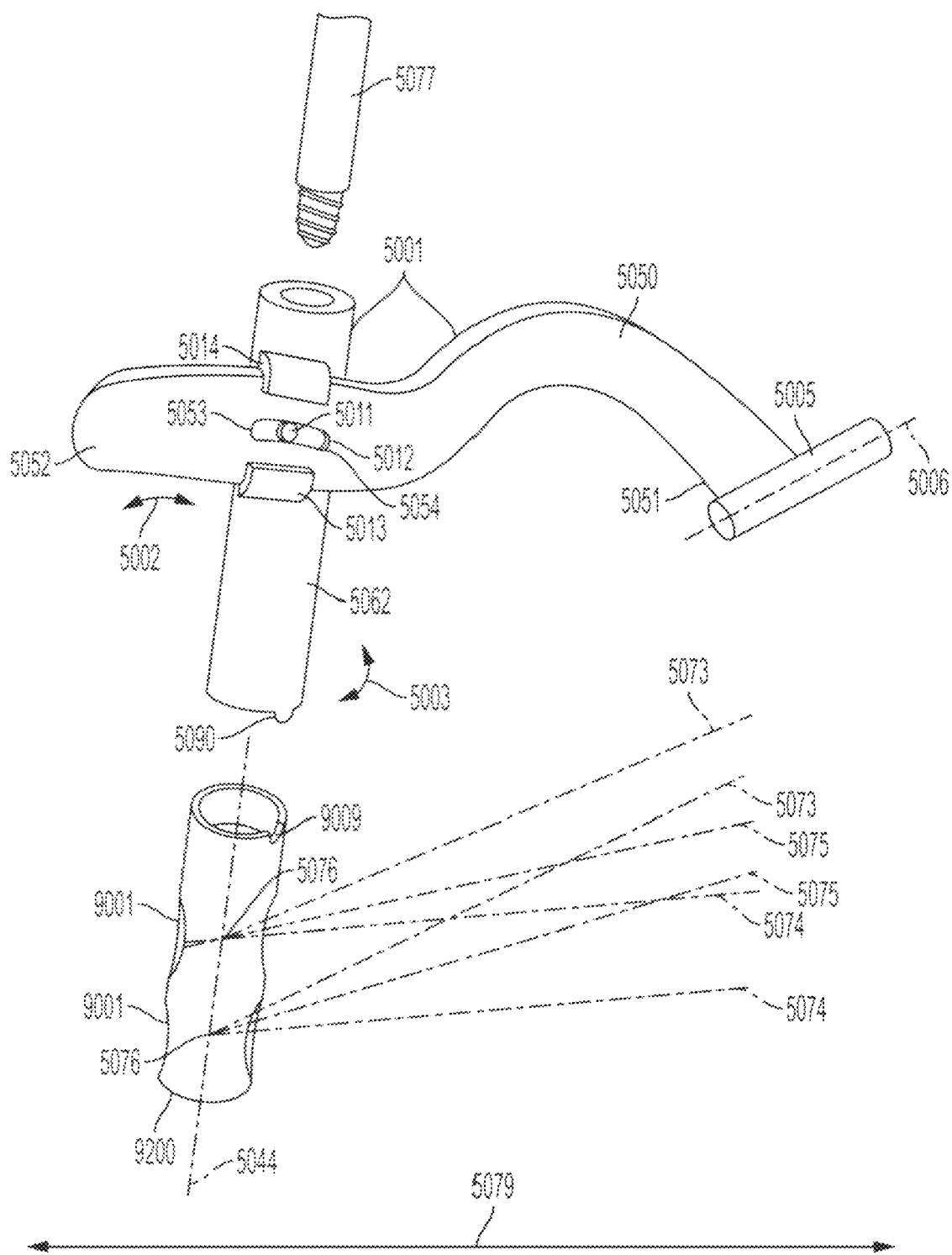
FIG. 26 is a disassembled side view an embodiment of a targeting guide with an adjustable arm.

Referring to FIG. 26, a targeting guide 5001 is shown along with post 9200, (see FIGS. 11-17) and a post fastener 5077. Targeting guide 5001 is shown with a post support member 5062 and an arm 5050. Arm 5050 has a first arm end 5052 and a targeting aperture 5005 connected to arm 5050, shown as a cylinder located at a second arm end 5051. Targeting aperture 5005 has a targeting axis 5006. A peg 5011 protrudes from post support member 5062 and through a slot 5012 in arm 5050. Slot 5012 may be curved. Arm 5050 is constrained between upper jaw 5014 and lower jaw 5013 and remains adjacent to and/or in contact with post support member 5062. Arm 5050 is movable in a vertical plane between the first arm end 5052 and second arm end 5051. However, the motion of arm 5050 is constrained by peg 5011. Peg 5011 is fixed to post support member 5062 and projects through arm slot 5012. Slot 5012 moves about peg 5011, with arm motion limited to the boundaries of slot 5012, as peg 5011 makes contact with and prevents motion past a first slot position 5053 and a second slot position 5054. Arm 5050 may slide between upper jaw 5014 and lower jaw 5013, leading to a rocking, forward and backward arm motion as curvature of slot 5012 moves along peg 5011. Being fixed to second arm end 5051, target aperture 5005 moves in line with the arm. The shape and movability of arm 5050 provide target aperture 5005 with targeting aperture positions that align targeting axis 5006 with a post aperture center point 5076, between an upper angle limit 5073 and a lower angle limit 5074, shown in relation to a post aperture axis 5075. Post aperture center point 5076 is at the intersection of a post longitudinal axis 5044 and post aperture axis 5075. Furthermore, lines depicting the upper angle limit 5073 and a lower angle limit 5074 may cross the post longitudinal axis 5044 at post aperture center point 5076. In this embodiment the motion of arm 5050 is coaxially along the length of arm 5050, where the arm length is depicted by line 5079, and in a vertical arc defined by positioning targeting axis 5006 between upper angle limit 5073 and lower angle limit 5074.

In this embodiment, post 9200 has post recess 9009 for connection with support member 5062 by inserting a tooth 5090 into recess 9009. There may be embodiments of post 9200 connected to guide 5001 without recess 9009 and without tooth 5090.

An embodiment of a post 1200 may be used with targeting guide 5001 and a suitable post fastener.

Figure 27A:
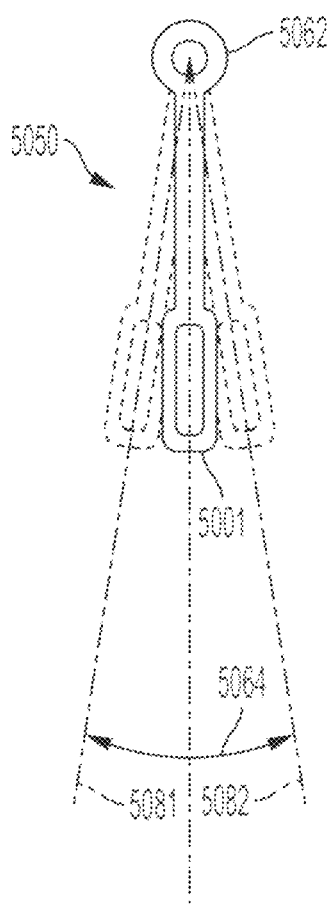
FIG. 27A depicts a top view of the targeting guide of FIG. 26 with a rotating arm.

A top view of a targeting guide 5001 with a post support member 5062 and an arm 5050 is depicted in FIG. 27A. Arm 5050 may be rotatable in a perpendicular arc about a post member longitudinal axis 5044 and through post support member 5062. In embodiments with post 9200 having recess 9009 and tooth 5090 inserted into recess 9009, rotation may be constrained to inhibit rotation. In other embodiments, the recess may be sized accordingly to provide for rotation of guide 5001 with respect to post 9200 and about post longitudinal axis 5044, between limits 5081 and 5082, and defining arc 5064.

Figure 27B:
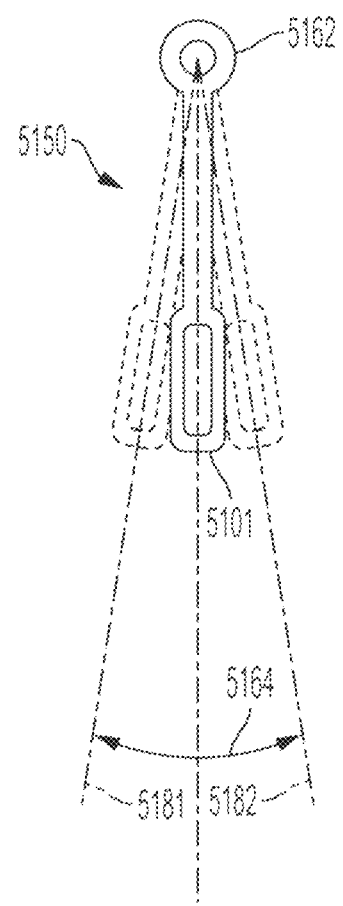
FIG. 27B is a top view of an embodiment of a targeting guide with a rotating arm.

Shown in FIG. 27B is a top view of a targeting guide 5101 with a post support member 5162 and an arm 5150. Arm 5150 may be rotatable in a perpendicular arc about a post support member longitudinal axis 5114 (see FIG. 28) through post support member 5162. Post support member longitudinal axis 5114 and post member longitudinal axis 5044 (See FIG. 26) may align. Arm 5150 may rotate between limits 5181 and 5182, defining an arc 5164.

Figure 28:
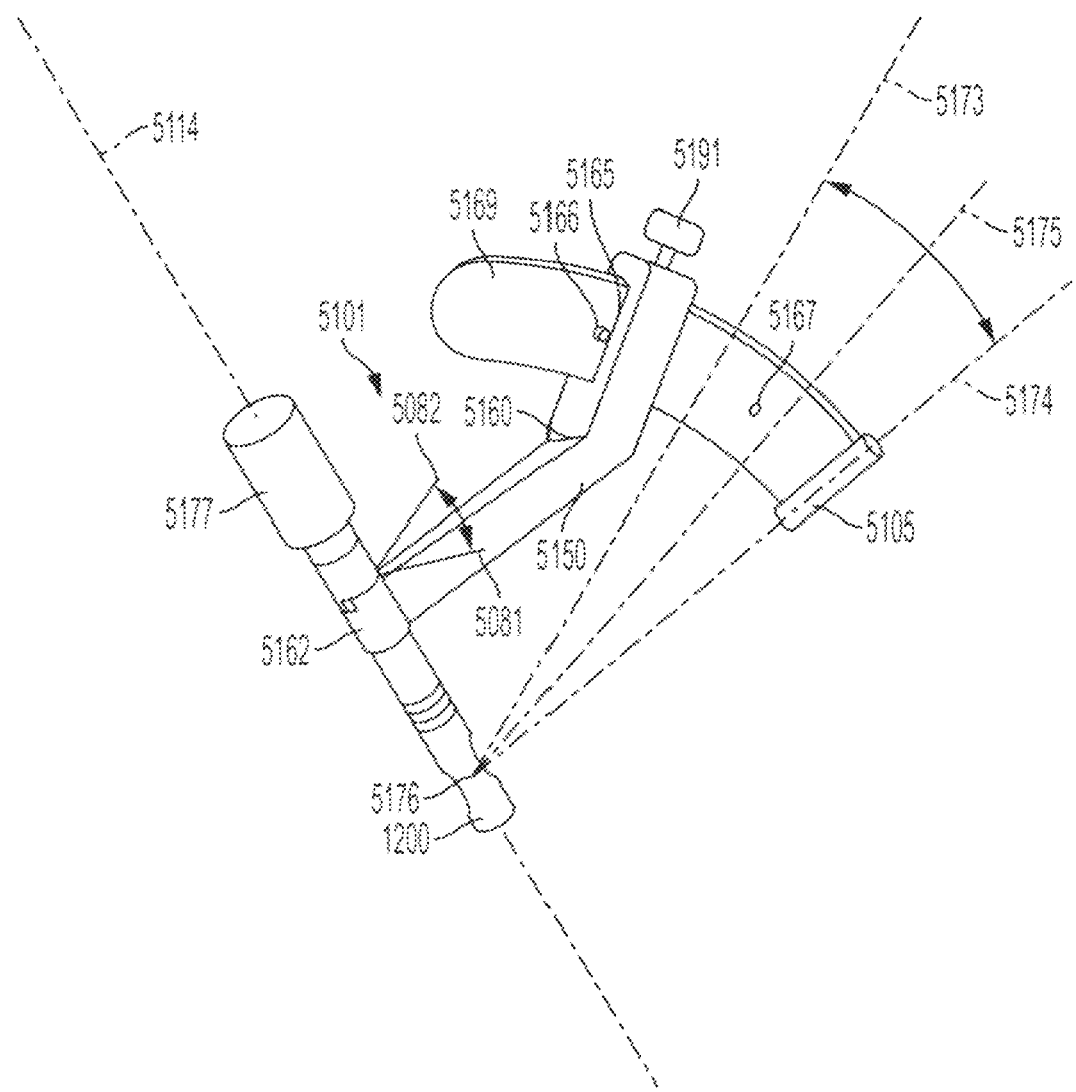
FIG. 28 depicts a perspective view of the targeting guide with a rotating arm of FIG. 27B with an adjustable leg.

Depicted in FIG. 28 is targeting guide 5101 with post 1200, and a post fastener 5177. In an alternate embodiment, post 9200 may be used instead of post 1200. Arm 5150 is rotatably connected to post support member 5162. Arm 5150 may be rotatable in a perpendicular arc relative to post support member longitudinal axis 5114 through post support member 5162. Rotation limits are between positions 5181 and 5182 (See FIG. 27B). Arm 5150 may have an upward angle or curvature at 5160 towards the end of arm 5150 distal to post support member 5162. A locking screw 5191 is connected to arm 5150. A leg 5169 is shown with a first peg 5166 and a second peg 5167 protruding through leg 5169. First peg 5166 and second peg 5167 may protrude through both sides of leg 5169 or may just extend out from 5169 on one side. Leg 5169 may slide through arm hole 5165 but is constrained by contact because neither first peg 5166 nor second peg 5167 may pass through arm hole 5165. The upper and lower limits are determined by the positions of first peg 5166 and second peg 5167 respectively. The position of leg 5169 between first peg 5166 and second peg 5167 may be locked in place by fastening locking screw 5191. Targeting aperture 5105 may be located at the end of leg 5169. By moving leg 5169 through arm hole 5165, an axis through targeting aperture 5105 and corresponding through a post aperture center point 5176 may be defined between positions 5173 and 5174. In this embodiment, post support member longitudinal axis 5114 is aligned with post longitudinal axis 5044 (see FIG. 26). Post aperture center point 5176 is at the intersection of post support member longitudinal axis 5114 and post aperture axis 5175. Furthermore, lines depicting the upper angle limit 5173 and a lower angle limit 5174 may cross the post longitudinal axis 5044 at post aperture center point 5176.

The curvature of arm 5150 varies with the application. Leg 5169 may have a curvature or it may be straight, depending on the application. The leg 5169 may also be straight or curved, depending on the application. Also, while a fastening lock screw is shown in the figures, other fasteners may be used in other embodiments.

Figure 29:
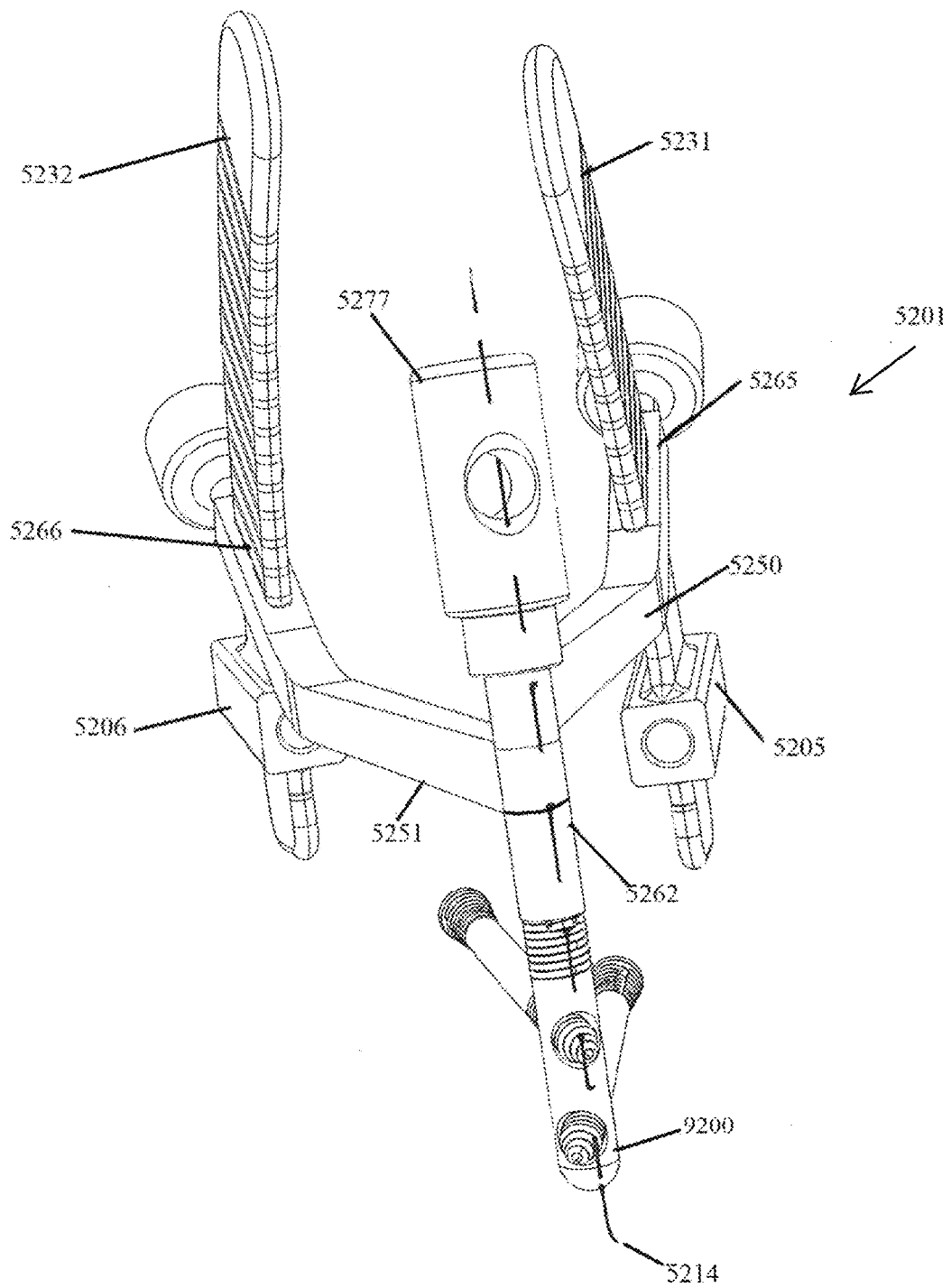
FIG. 29 is a front view of a targeting guide with two arms.
Figure 30:
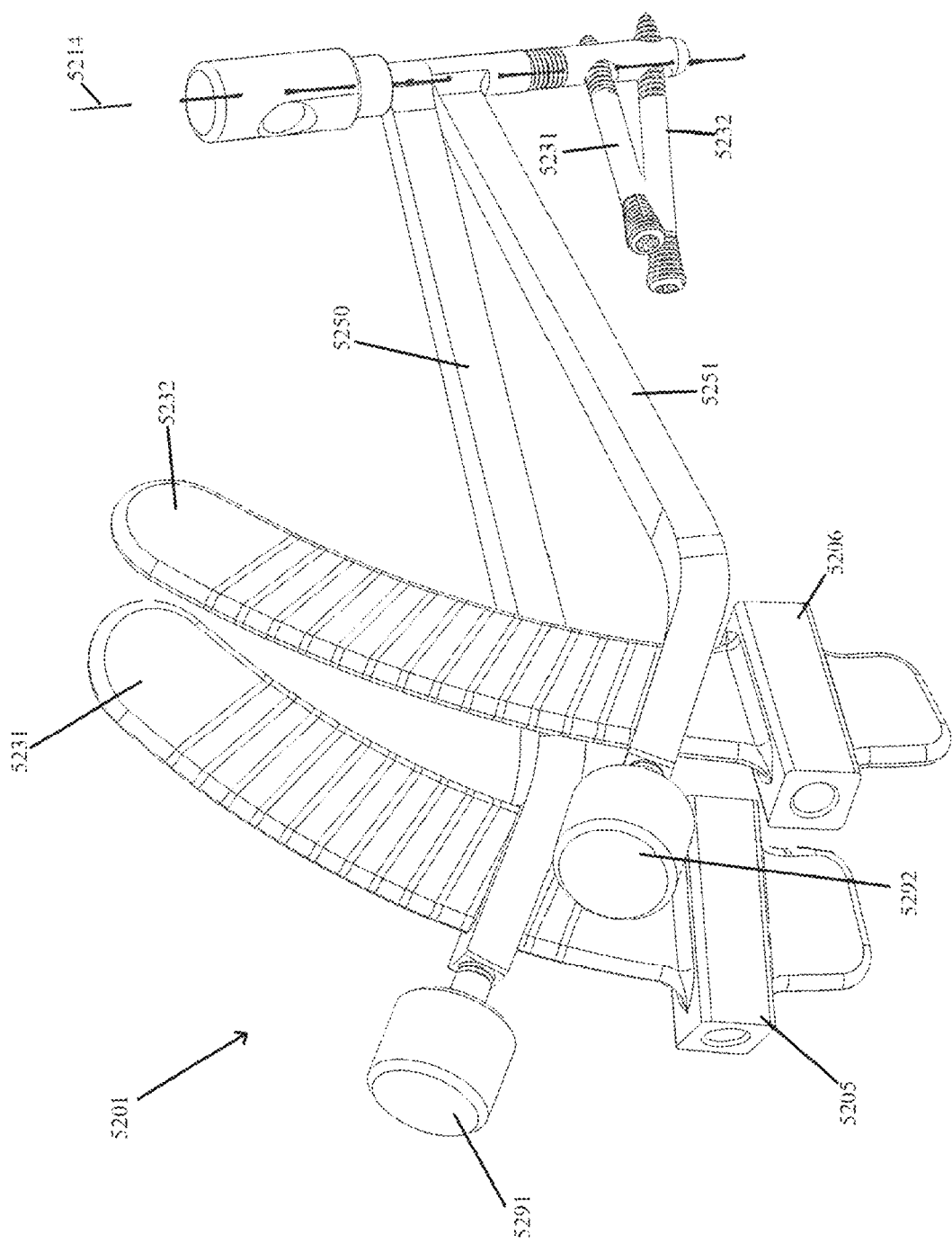
FIG. 30 depicts a rear perspective view of the targeting guide with two arms of FIG. 29.
Figure 31:
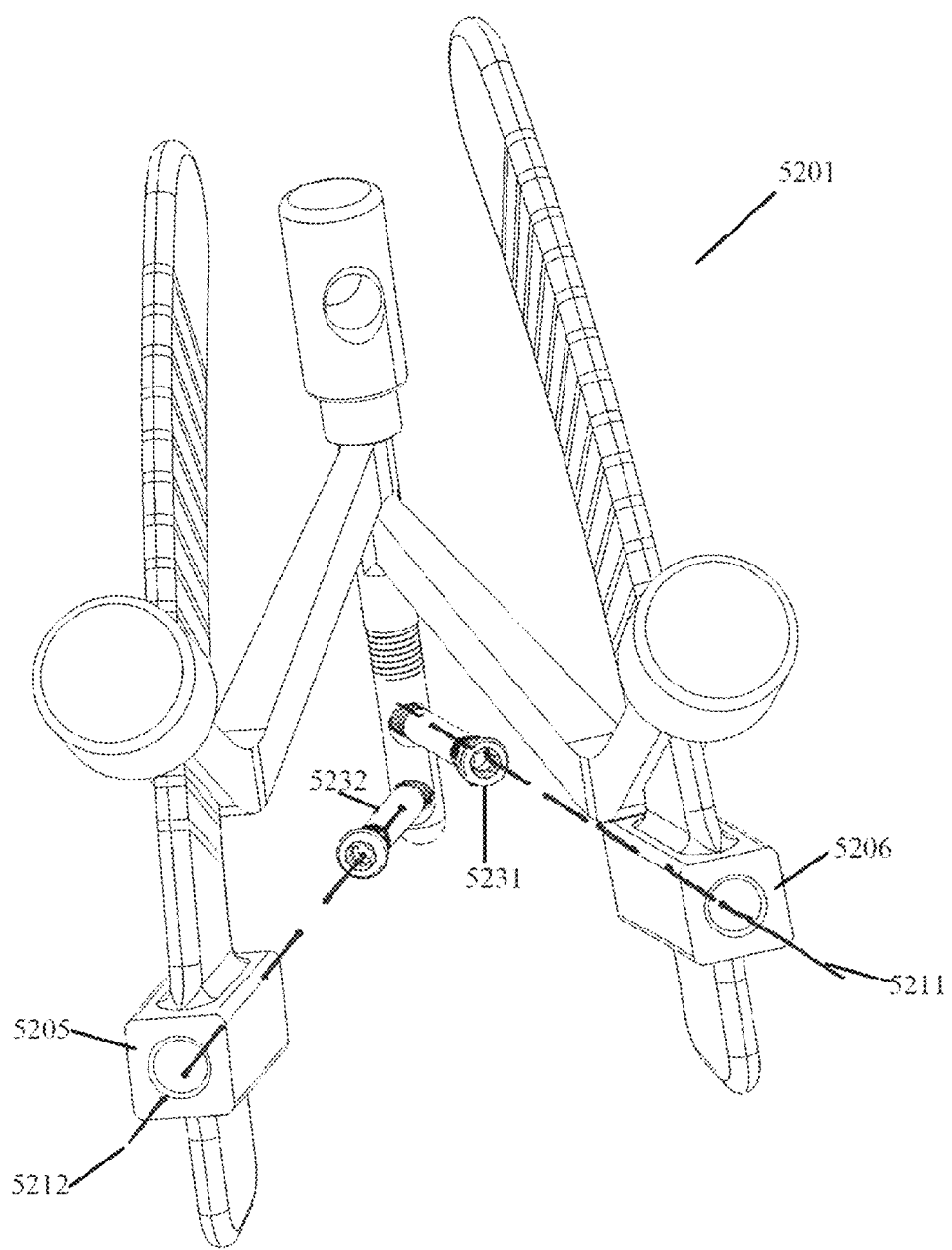
FIG. 31 depicts a rear view of the targeting guide with two arms of FIG. 29.

FIG. 29-31, depict various views of targeting guide 5201. Targeting guide 5201 is shown along with post 9200, and a post fastener 5277. Targeting guide 5201 is shown with a first arm 5250, and a second arm 5251. First arm 5250 and second arm 5251 are rotatably connected to post support member 5262, with first arm 5250 shown connected above second arm 5251 forming a hinge about post fastener 5277, where post fastener 5277 is releasably connected to post 9200. First arm 5250 may be horizontally rotatable in a longitudinally perpendicular direction to a post longitudinal axis 5214, through post 9200, through post support member 5262, through arms 5250 and 5251, and post fastener 5277. Second arm 5251 may be horizontally rotatable in a longitudinally perpendicular direction relative to post longitudinal axis 5214 through post 9200, through post support member 5262, through first arm 5250, second arm 5251, and post fastener 5277.

Further referring to FIGS. 29-31, first leg 5231 passes through a first arm hole 5265 and is fastened in place by a first fastening lock screw 5291. Second leg 5232 passes through a second arm hole 5266 and is fastened in place by a second fastening lock screw 5292. First leg 5231 is connected to a first target aperture 5205. Second leg 5232 is connected to a second target aperture 5206. Each leg may be adjusted by releasing the corresponding fastening lock screw and moving the leg up or down. First targeting aperture 5205 has a first targeting aperture axis 5212, which may be aligned with an appropriate post aperture axis for placement of a first screw 5232. Second targeting aperture 5206 has a second targeting aperture axis 5211, which may be aligned with an appropriate post aperture axis for placement of a second screw 5231. The arms are shown as having a straight portion, extending from post support member 5262, and a curved portion longitudinally towards the distal end of the arms.

Generally referring to FIGS. 29-31, first arm 5250 and second arm 5251 are shown rotatably connected to post support member 5262, with first arm 5250 shown connected above second arm 5251. First arm 5250 and second arm 5251 may be configured so that second arm 5251 may be rotatably affixed to post support member 5262 while first arm 5250 may have a removable sleeve which stacks onto post support member 5262. Such a configuration would allow a plurality of arms to be stacked vertically onto second arm 5251. Further configurations and connections that would allow at least two arms to be configured in any way to rotate about post support member 5262. Post support member, first arm 5250, and second arm 5251 may each have a bore, so when stacked, the post longitudinal axis 5214 passes coaxially, and post fastener 5277 may pass therethrough to connect to post 9200. Post support member 5262 may have a tubular extension upon which second arm 5251, first arm 5250, and through which post fastener 5277 may pass to connect to post 9200. Post 9200 may generally have six or less apertures 9001, which would correspond to targeting guide 5201 having six arms vertically stacked. There may be embodiments of post 9200, with more than six apertures.

Post 9200 may be configured to be releasably connected (i.e. inhibiting rotation and translation with respect) to targeting guide 5201 that directs instrumentation to the post apertures 9001 with internal threading or internal engagement structures (see FIGS. 11-17). However, in embodiments shown in FIGS. 29-31, while post 9200 is connected to targeting guide 5201, first arm 5250 and second arm 5251 may be movable with respect to post 9200. Post 9200 connects to targeting guide 5201 at post support member 5262. Targeting guide 5201 may be releasable from the post 9200 by removing a post fastener 5277.

Generally referring to FIG. 29-31, the arms may be straight, curved or angled depending on the application. The legs may also be straight or curved in some embodiments. Also, while a fastening lock screw is shown in the figures, other fasteners may be used in other embodiments.

Figure 32:
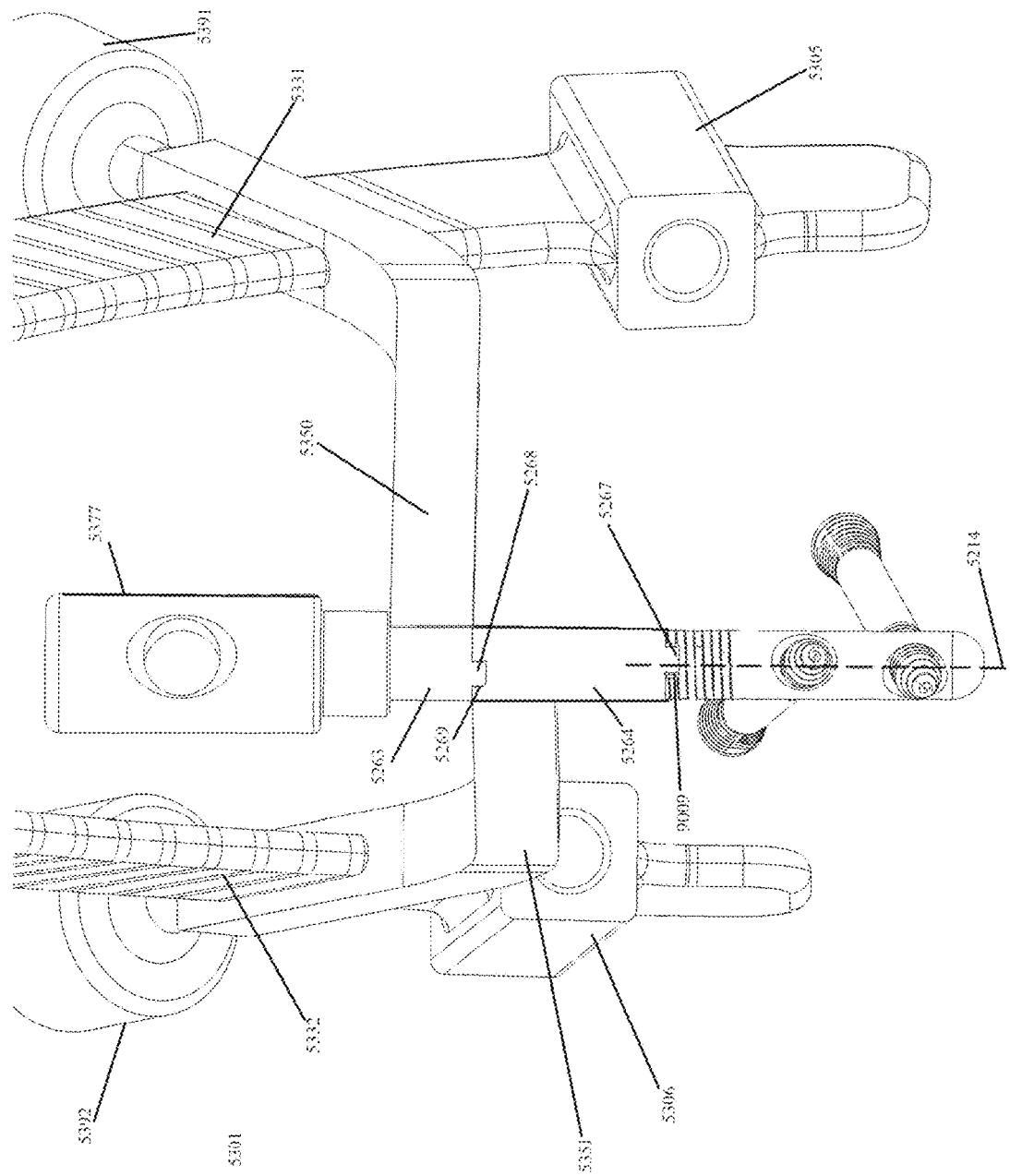
FIG. 32 is a front view of an embodiment of a targeting guide with two arms and connected post with teeth and recesses.

FIG. 32 depicts a targeting guide 5301 connectable with post 9200 having recess 9009. Post 9200 is configured to be releasably connected (i.e. inhibiting rotation and translation with respect) to targeting guide 5301 that directs instrumentation to the post apertures 9001 with internal threading or internal engagement structures (see FIGS. 11-17). Post 9200 connects to targeting guide 5301 at second arm connection 5264, with first arm connection 5263 positioned above, and with post 9200. Second arm 5351 and first arm 5350 may be releasably connected by post fastener 5377. As post fastener 5377 is connected to post 9200, post longitudinal axis 5214 may pass coaxially through post fastener 5377. Second arm 5351 has a second arm tooth 5267 slotted within recess 9009. First arm 5350 has a first arm tooth 5268 slotted within a second arm recess 5269. In this configuration, first arm 5350 and second arm 5351 are in fixed relation to each other and post 9200, but are together rotatable about post longitudinal axis 5214. Additional targeting guides arms may be coupled in the same way, with additional upper components requiring a similar tooth (e.g. first arm tooth 5268) to restrict the movement of the arms (e.g. first arm 5350 and second arm 5351) with respect to each other. The number of arms may depend on the number of apertures in a post to which screws are intended to be connected. Post 9200 may generally have six or less apertures 9001, which would correspond to targeting guide 5301 having six arms vertically stacked and constrained by a respective recess and tooth configuration. There may be embodiments of post 9200, with more than six apertures.

Referring to FIG. 32, each tooth (e.g. second arm tooth 5268), extending substantially vertically parallel to post longitudinal axis 5214 from each arm connection (e.g. second arm connection 5263), may fit into a respective recess (e.g. second arm recess 5269) to eliminate rotation and translation of arms with respect to each other, and with respect to post 9200. Further post fastener 5377 may be configured to lock the permissible rotation when fully tightened, or a washer may be included as a separate locking step to eliminate all movement of the guide with respect to the post. Alternatively, each tooth may fit into its respective recess, with the recess horizontally (i.e. in a perpendicular arc about post longitudinal axis) sized to allow limited rotation of arms, with respect to each other, about post longitudinal axis 5214.

FIG. 32 depicts targeting guide 5301 with curved arms. Other embodiments may have angled arms or straight arms. First arm 5350 extends from first arm connection 5264, perpendicularly to post longitudinal axis 5214. A curvature or angling of first arm 5350 may be towards the distal end of first arm 5350 from the first arm connection 5264 and along the length of arm 5350. Second arm 5351 extends from first arm connection 5263, perpendicularly to the post longitudinal axis 5214. A curvature or angling of second arm 5301 may be towards the distal end of second arm 5351 from the second arm connection 5263 and along the length of arm 5351.

Further referring to FIG. 32, in an embodiment where first arm 5350 and second arm 5351 are fixed in relation to each other, trajectory adjustments may be made by moving a first leg 5331 through first arm 5350, thereby moving a first targeting aperture 5305, and a second leg 5332 through second arm 5351, thereby and a second targeting aperture 5306. A first lock screw 5391 and a second lock screw 5392 may be used to lock first leg 5331 and second leg 5332 respectively into place.

Figure 33:
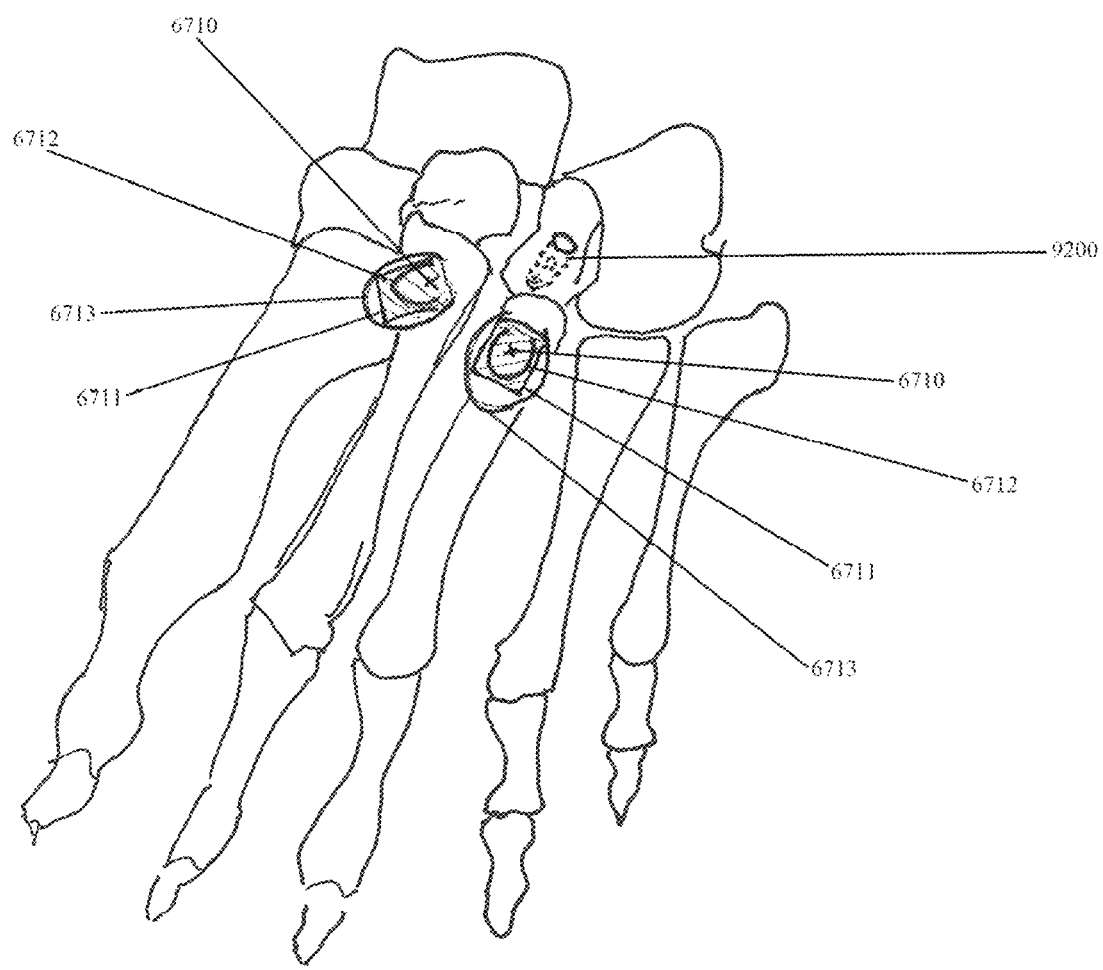
FIG. 33 depicts a foot viewed from the distal dorsal to proximal plantar, with a post placed in the lateral cuneiform bone and with permissible targeting regions.

FIG. 33 depicts the bones of the foot viewed from the distal dorsal to proximal plantar, with post 9200 placed in the lateral cuneiform bone. Further depicted is a first zone 6711, a first arc 6712, a second arc 6713, and an aperture axis 6710. The aperture axis 6710 is axially visible and is depicted as a cross.

Referring to FIGS. 26-33, first zone 6712 represents a rectangular area in which screw placement may be made for connection with post 9200, using targeting aperture 5005 of targeting guide 5001, targeting aperture 5105 of targeting guide 5101, targeting aperture 5205 and targeting aperture 5206 of targeting guide 5201, and targeting aperture 5305 and targeting aperture 5306 of targeting guide 5301. The rectangular area of first zone 6712 may vary in size for each guide indicated above and for each particular application (e.g. Lisfranc procedure, Lapidus procedure, or other bone fusion procedure).

A first arc 6712 and a second arc 6713 represent arcs along which screw placement may be made for connection with post 9200, using a targeting guide offset 7101 with targeting apertures 6070 of targeting guide 6100. First arc 6712 is defined by a smaller offset used with targeting guide 6100. Second arc 6713 is defined by a larger offset used with targeting guide 6100.

Generally referring to FIGS. 1-33, targeting apertures 3300, 6070, 5005, 5105, 5205, 5206, 5305, 5306, and any other embodiment of a targeting apertures may include but is not limited to, a single aperture, a tube or a cylinder, a double aperture separated by a distance, or any targeting structure or sighting structure which facilitates targeting a post engagement structure removed from the targeting aperture.

Referring to FIGS. 1-33, targeting guides 3000, 6100, 5001, 5101, 5201, and 5301 may be used with post 1200, post 9200 or any other embodiment of a post. Furthermore, targeting guides 3000, 6100, 5001, 5101, 5201, 5301 may be used with targeting offset 7101 or any of its embodiments.

Referring generally to FIGS. 1-33, post fasteners 5377, 5277, 5177, 5077, 1577 or a similar embodiment may be used with targeting guide 6100.

Referring to FIGS. 3 and 20, targeting guide 3000 is depicted with compression-distraction fixture 3600. Compression distraction fixture 3600 may be connected to any of targeting guides 6100, 5001, 5101, 5201, and 5301 for similar use as described in this application.

Referring to FIGS. 29-32, first peg 5166 and second peg 5167 (FIG. 28) or similar structures may be present to limit the motion of targeting guide legs through arm holes (e.g. first arm hole 5265). Friction and flaring may alternatively by used to limit motion of targeting guide legs through arm holes (e.g. first arm hole 5265).

Referring to FIGS. 1-33, embodiments of targeting guides 3000, 6100, 5001, 5101, 5201, 5301 using post 9200 with recess 9009, may also have corresponding teeth (e.g. second arm tooth 5267), which may slot into recess 9009 to inhibit arm rotation relative to post 9200. There may be embodiments of targeting guides 5201 and 5301, using post 9200 with recess 9009, which may inhibit movement of a targeting arm (e.g. second arm 5251) directly above post 9200, with respect to post 9200, but allow arms stacked vertically to rotatably move relative to the post 9200 and relative to the targeting arm directly above post 9200.

FIGS. 18-23 depict the use of targeting guide 3000 and post 1200 in various applications. Targeting guides 6100, 5001, 5101, 5201, and 5301 may similarly be used with either post 9200 or 1200, as depicted in FIGS. 18-23. Each of the embodiments for a targeting guides described herein may be used to seat a post into a medial cuneiform or an operationally similar bone, as required by surgical procedure. Targeting guides 5001, 5101, 5201, and 5301 have movable arms, some of which rotate, and which provide for trajectory adjustment in the positioning and placement of bushings 3175, drill bits 3170, and screws 1100. Targeting guides connected to movable legs and movable targeting apertures provide for greater positional refinement and improved trajectory of bushings 3175, drill bits 3170, and screws 1100. Most commonly, targeting guides 6100, 5001, 5101, 5201, and 5301 may be used with post 9200. The preferred use of movable arms and targeting apertures may be for selecting the trajectory in which to drill and place the screws for connection to the post to maximizing the amount of bone surrounding an implant (i.e. post and connected screws). An alternate use for movable arms and targeting apertures is for selecting a trajectory that avoid other existing hardware. The use of a post that may catch a screw thread despite a sub-optimal or offset placement in relation to a post aperture may also aid in selecting better bone thickness and avoiding hardware in screw placement.

The various embodiments described herein provide for targeting guides and posts that optimize a screw trajectory for intersecting the post aperture and optimizes considerations for anatomy and construct stability in promoting bone fusion.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopedic instrument assembly for placing an implant into a bone, the assembly comprising:
    a targeting guide comprising an adjustable targeting arm having a targeting aperture, wherein the targeting aperture defines a targeting axis through the targeting aperture;
    a post having a longitudinal axis and the post connectable to the targeting guide;
    the post comprising a post aperture and a post aperture center;
    wherein the post aperture defines a post aperture axis through the post aperture, the post aperture axis intersecting the longitudinal axis at the post aperture center;
    the adjustable targeting arm movable to align the targeting axis with the post aperture center and thereby align the targeting aperture with the post aperture;
    the adjustable targeting arm rotatably connected to a post support, the targeting arm movable in an arc about the post support; and
    the adjustable targeting arm connected to an adjustable leg movable relative to the arm;
    the adjustable targeting arm comprising an arm hole, the adjustable leg passing through said arm hole, and a fastener;
    the adjustable leg connected to the targeting aperture;
    a second adjustable targeting arm rotatably connected to the post, the second adjustable targeting arm comprising a second arm hole, a second adjustable leg passing through said second arm hole and a second fastener; and
    the second adjustable leg connected to a second targeting aperture.

2. The orthopedic instrument assembly of claim 1, wherein the targeting guide further comprises a post support; wherein the adjustable targeting arm has a first arm end, a connection to the post support, and a second arm end; and wherein the targeting aperture is connected to the second arm end and the adjustable targeting arm is movable along the connection between a first position and a second position.

3. An orthopedic instrument assembly for placing an implant into a bone, the assembly comprising:

a targeting guide comprising an adjustable targeting arm and a targeting aperture, wherein the targeting aperture defines a targeting axis through the targeting aperture;

a post having a longitudinal axis and the post connectable to the targeting guide;

the post comprising a post aperture and a post aperture center; said post aperture defining a post aperture axis through the post aperture, the post aperture axis intersecting the longitudinal axis at the post aperture center, and comprising at least one internal engagement structure, said internal engagement structure configured for a plurality of alignments of a screw for engaging the post;

the adjustable targeting arm rotatably movable to align the targeting axis with the post aperture center and thereby align the targeting aperture with the post aperture;

said post aperture comprising a tapered opening, the tapered opening angled to guide the screw to the at least one internal engagement structure.

4. The orthopedic instrument assembly of claim 3, wherein the adjustable targeting arm has a first arm end, a connection to a post support, and a second arm end; wherein the targeting aperture is connected to the second arm end and the adjustable targeting arm is movable along the connection between a first position and a second position.

5. The orthopedic instrument assembly of claim 4 wherein the arm is rotatable between a first arc position and a second arc position.

6. The orthopedic instrument assembly of claim 3, wherein the adjustable targeting arm is rotatably connected to a post support, the targeting arm movable in an arc about the post support.

7. The orthopedic instrument assembly of claim 6, wherein the adjustable targeting arm further comprises an arm hole, an adjustable leg passing through said arm hole, and a fastener; and wherein the adjustable leg is connected to the targeting aperture.

8. The orthopedic instrument assembly of claim 6 wherein the arm is rotatable between a first arc position and a second arc position; and wherein the targeting aperture is movable between a first targeting aperture position and a second targeting aperture position.

9. The orthopedic instrument assembly of claim 3 further comprising a second adjustable targeting arm; wherein the adjustable targeting arm is rotatably connected to a post support, the targeting arm movable in an arc about the longitudinal axis; and wherein the second adjustable targeting arm is rotatably connected to the adjustable targeting arm, the second targeting arm movable in an arc about the post support.

10. The orthopedic instrument assembly of claim 9 wherein the adjustable targeting arm further comprises an arm hole, an adjustable leg passing through said arm hole, and a fastener; and wherein the adjustable leg is connected to the targeting aperture; and wherein the second adjustable targeting arm further comprises a second arm hole, a second adjustable leg passing through said second arm hole, and a second fastener; and wherein the second adjustable leg is connected to a second targeting aperture.

11. The orthopedic instrument assembly of claim 9 wherein the post further comprising a recess, the adjustable targeting arm further has a tooth, and wherein the tooth is insertable in the recess constraining the targeting arm such that the post is statically, releasably connectable to the targeting guide such that the targeting guide and the post are rotatably moveable about the longitudinal axis.

12. The orthopedic instrument assembly of claim 11 wherein the adjustable targeting arm further has a targeting arm recess, the second targeting arm further has a second arm tooth, and wherein the second arm tooth is insertable in the targeting arm recess, constraining the second targeting arm relative to the adjustable targeting arm.

13. The post of claim 3 wherein the at least one internal engagement structure engages or partially engages a threading of the screw.

14. The post of claim 3 wherein the at least one internal engagement structure substantially matches a threading pitch of the screw.

15. The post of claim 3 wherein the at least one internal engagement structures comprise planar members extending radially inward in a plane perpendicular to a circumference of the aperture.

16. The post of claim 3 wherein the at least one internal engagement structure has compliant planar members providing for at least near engagement with threading of the screw, wherein the compliant planar members are movable with respect to a primary axis of the screw, and moving the screw into the post aperture.

17. The post of claim 3 wherein said post aperture comprises a tapered opening, the tapered opening angled to guide the screw to the at least one internal engagement structure; wherein the at least one internal engagement structure engages or partially engages a threading of the screw; and wherein the at least one internal engagement structure substantially matches a threading pitch of the screw.

18. The post of claim 17 wherein said post apertures have a post aperture axis, and wherein the at least one internal engagement structures provide for approach angles for the screw of 0 degrees to 20 degrees offset from the post aperture axis.

19. An orthopedic instrument assembly for placing an implant into a bone, the assembly comprising:
a targeting guide comprising an adjustable targeting arm having a targeting aperture, wherein the targeting aperture defines a targeting axis through the targeting aperture;
a post having a longitudinal axis and the post connectable to the targeting guide;
the post comprising a post aperture and a post aperture center;
wherein the post aperture defines a post aperture axis through the post aperture, the post aperture axis intersecting the longitudinal axis at the post aperture center;
the adjustable targeting arm movable to align the targeting axis with the post aperture center and thereby align the targeting aperture with the post aperture;
the adjustable targeting arm rotatably connected to the post, the targeting arm movable in an arc about the longitudinal axis; and
a second adjustable targeting arm, the second adjustable targeting arm rotatably connected to adjustable targeting arm, the second targeting arm movable in an arc about the longitudinal axis.

20. An orthopedic instrument assembly for placing an implant into a bone, the assembly comprising:
a targeting guide comprising an adjustable targeting arm and a targeting aperture, the targeting aperture defining a targeting axis through the targeting aperture;
a post having a longitudinal axis and the post connectable to the targeting guide;
the post comprising a post aperture and a post aperture center; said post aperture defining a post aperture axis through the post aperture, the post aperture axis intersecting the longitudinal axis at the post aperture center, and comprising at least one internal engagement structure, said internal engagement structure configured for a plurality of alignments of a screw for engaging the post;

the adjustable targeting arm rotatably movable to align the targeting axis with the post aperture center and thereby align the targeting aperture with the post aperture;

the at least one internal engagement structures having compliant planar members providing for at least near engagement with threading of the screw, the compliant planar members movable with respect to a primary axis of the screw, and configured to move the screw into the post aperture.

21. An orthopedic instrument assembly for placing an implant into a bone, the assembly comprising:

a targeting guide comprising an adjustable targeting arm and a targeting aperture, the targeting aperture defining a targeting axis through the targeting aperture;

a post having a longitudinal axis and the post connectable to the targeting guide;

the post comprising a post aperture and a post aperture center; said post aperture defining a post aperture axis through the post aperture, the post aperture axis intersecting the longitudinal axis at the post aperture center, and comprising at least one internal engagement structure, said internal engagement structure configured for a plurality of alignments of a screw for engaging the post;

the adjustable targeting arm rotatably movable to align the targeting axis with the post aperture center and thereby align the targeting aperture with the post aperture;

said post aperture comprising a tapered opening, the tapered opening angled to guide the screw to the at least one internal engagement structure;

the at least one internal engagement structure engaging or partially engaging a threading of the screw; and the at least one internal engagement structure substantially matching a threading pitch of the screw.

* * * * *